United States Patent
Berneth et al.

(10) Patent No.: US 6,545,793 B2
(45) Date of Patent: Apr. 8, 2003

(54) UV-PROTECTED ELECTROCHROMIC SOLUTION

(75) Inventors: Horst Berneth, Leverkusen (DE); Helmut-Werner Heuer, Krefeld (DE); Ralf Neigl, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/037,398

(22) Filed: Jan. 3, 2002

(65) Prior Publication Data

US 2002/0145790 A1 Oct. 10, 2002

Related U.S. Application Data

(62) Division of application No. 09/485,660, filed as application No. PCT/EP98/04910 on Aug. 6, 1998, now Pat. No. 6,372,159.

(30) Foreign Application Priority Data

Aug. 18, 1997 (DE) .......................... 197 35 732

(51) Int. Cl.$^7$ ................................. G02F 1/15
(52) U.S. Cl. ................ 359/265; 359/242; 359/245; 359/267; 359/275
(58) Field of Search ............ 359/265–75; 345/49, 345/105; 252/582, 583, 586; 348/817

(56) References Cited

U.S. PATENT DOCUMENTS

| | | | | |
|---|---|---|---|---|
| 3,280,701 A | | 10/1966 | Donnelly et al. ............ 359/267 |
| 4,902,108 A | | 2/1990 | Byker ........................ 359/265 |
| 5,239,406 A | * | 8/1993 | Lynam ....................... 359/275 |
| 6,157,479 A | * | 12/2000 | Heuer et al. ................ 359/265 |
| 6,183,878 B1 | * | 2/2001 | Berneth et al. ............. 428/583 |

FOREIGN PATENT DOCUMENTS

| | | | | |
|---|---|---|---|---|
| DE | WO-9730134 | * | 8/1997 | |
| EP | 0 435 689 | | 7/1991 | ............ C09K/9/02 |

OTHER PUBLICATIONS

Topics in Current Chemistry, vol. 92, pp. 1–44, (month unavailable) 1980, Hünig et al Two Step Reversible Redox Systems of the Weitz Type.

Angew. Chem. 90, (month unavailable) 1978, pp. 927–938 (English language translation attached also), Deuchert et al, Mehrstufige organische Redoxsysteme–ein allgemeines Strukturprinzip.

* cited by examiner

*Primary Examiner*—Jordan M. Schwartz
*Assistant Examiner*—Jessica Stultz
(74) *Attorney, Agent, or Firm*—Godfried R. Akorli; Richard E. L. Henderson; Diderico van Eyl

(57) ABSTRACT

This invention relates to electrochromic devices containing UV-protected electrochromic solutions comprising at least one oxidizable substance $RED_1$ and at least one reducible substance $OX_2$ linked by a bridging group and a UV absorber component.

6 Claims, No Drawings

UV-PROTECTED ELECTROCHROMIC SOLUTION

This application is a Divisional of Ser. No. 09/485,660 filed Feb. 14, 2000, now U.S. Pat. No. 6,372,159 which is a 371 of PCT/EP98/04910 filed Aug. 6, 1998.

The present invention relates to a UV-protected electrochromic solution, to its use in an electrochromic device and to an electrochromic device comprising this solution.

Electrochromic devices comprising an electrochromic system are already known.

The electrochromic system of such devices customarily includes pairs of redox substances—redox couples—dissolved in an inert solvent. Additionally, conductive salts, light stabilizers and substances which influence the viscosity may be present The redox couple used comprises one reducible and one oxidizable substance each. Both are colourless or have only a weak coloration. Under the influence of an electrical voltage the one substance is reduced and the other oxidized, with at least one becoming coloured in the process. After the voltage is switched off, the two original redox substances are formed once more, which is accompanied by the disappearance or fading of the colour.

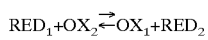

$$RED_1 + OX_2 \rightleftarrows OX_1 + RED_2$$

(colourless) (coloured)

(low-energy couple) (high-energy couple)

U.S. Pat. No. 4,902,108 discloses that suitable such redox couples are those in which the reducible substance has at least two chemically reversible reduction waves in the cyclic voltammogram and the oxidizable substances, correspondingly, has at least two chemically reversible oxidation waves.

Electrochromic devices can find multifarious applications. For example, they may take the form of a car rearview mirror which when travelling at night can be darkened by applying a voltage, thus preventing the driver being dazzled by headlights of other vehicles (cf. e.g. U.S. Pat. No. 3,280,701, U.S. Pat. No. 4,902,108, EP-A-0 435 689). Such devices may also be employed in window panes or car sun-roofs where, following the application of a voltage, they provide shade from the sunlight. Finally, it is possible to use such devices to construct a display device for the graphic representation of information in the form of letters, numbers and symbols.

Electrochromic devices normally consist of a pair of glass or plastic plates, one being mirrored in the case of a car mirror. One side of these plates is coated with a transparent, electroconductive layer, e.g. indium tin oxide (ITO). These plates are then used to construct a cell; to this end their facing, electroconductively coated side is attached, preferably by means of adhesive bonding, to an annular or rectangular sealing ring. The sealing ring establishes a uniform distance between the plates of, for example, from 0.1 to 0.5 mm. This cell is then filled, via an aperture, with an electrochromic solution and then tightly sealed. By way of the ITO layer it is possible to contact the two plates separately.

The electrochromic systems known from the prior art comprise redox couples which following the reduction and oxidation, respectively, form coloured free radicals, cationic free radicals or anionic free radicals that are chemically reactive. As known, for example, from Topics in Current Chemistry, Vol. 92, pp. 1–44 (1980) such (ionic) free radicals may be sensitive to electrophiles or nucleophiles or else to free radicals. In order, therefore, to achieve a high level of stability in an electrochromic device comprising an electrochromic system of this kind—a system which is intended to withstand several thousand switching cycles—it is necessary to ensure that the solvent used is absolutely free from electrophiles, e.g. protons, nucleophiles and oxygen. It must also be ensured that such reactive species are not formed by electrochemical processes taking place at the electrodes during operation of the electrochromic device.

The back-reaction to $RED_1$ and $OX_2$ that is formulated in the above equation also takes place continuously away from the electrodes within the volume of the solution while the electrochromic device is in operation. Owing to the above-described hazards of degradation reactions of the (ionic) free radicals by electrophiles, nucleophiles or free radicals it is important, for the long-term stability of the display, that the back-reaction in accordance with the above equation is able to take place as rapidly as possible and without side reactions.

Electrochromic devices of this kind generally exhibit sensitivity to light, especially UV light. Consequently, electrochromic devices have been disclosed which comprise UV stabilizers, for example in U.S. Pat. No. 5,280,380.

It has now been found that by coupling $RED_1$ and $OX_2$ by way of a covalent chemical bond the electron transfer is facilitated and thus the back-reaction indicated in the above equation can be accelerated and side reactions avoided.

It has likewise been found that electrochromic solutions comprising such $RED_1$ and $OX_2$ bridged via a covalent chemical bond can be effectively protected by particular UV absorbers against destruction by UV light.

The present invention accordingly relates to an electrochromic solution comprising at least one oxidizable substance $RED_1$ which releases electrons at an anode, and at least one reducible substance $OX_2$ which accepts electrons at a cathode and in so doing undergo transition from a weakly coloured or colourless form into a coloured form $OX_1$ and $RED_2$, respectively, accompanied by an increase in the absorbance in the visible region of the spectrum, the weakly coloured or colourless form being restored after charge equalization, characterized in that at least one of the substances $RED_1$ and $OX_2$ that are present are linked covalently to one another via a bridge and in that there is at least one UV absorber selected from the classes of the unsubstituted and substituted cinnamic esters and of the unsubstituted and substituted 2-hydroxybenzophenones. At least one of the oxidation- or reduction-induced transitions $RED_1 \rightleftarrows OX_1$ or $OX_2 \rightleftarrows RED_2$, respectively, is associated with an increase in the absorbance in the visible region of the spectrum.

The reduction and oxidation processes in the electrochromic system of the invention generally take place by electrons being accepted or released at a cathode or anode, respectively, a potential difference of from 0.3 to 3 V preferably obtaining between the electrodes. After the electrical potential has been switched off, charge equalization takes place—in general spontaneously—between the substances $RED_2$ and $OX_1$, accompanied by disappearance or fading of the colour. Such charge equalization also takes place even while the current is flowing in the interior of the electrolyte volume.

The electrochromic solution of the invention preferably comprises at least one electrochromic substance of the formula (I)

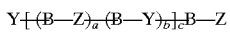   (I), in which
- Y and Z independently of one another represent a radical $OX_2$ or $RED_1$, subject to the proviso that at least one Y represents $OX_2$ and at least one Z represents $RED_1$, where
- $OX_2$ represents the radical of a reversibly electrochemically reducible redox system, and
- $RED_1$ represents the radical of a reversibly electrochemically oxidizable redox system,
- B represents a bridge
- c represents an integer from 0 to 5, and
- a and b independently of one another represent an integer from 0 to 5, preferably an integer from 0 to 3, and at least one UV absorber selected from the classes of the unsubstituted and substituted cinnamic esters and of the unsubstituted and substituted 2-hydroxybenzophenones.

The electrochromic solution preferably comprises at least one electrochromic substance of the formula (I) in which
- Y represents $OX_2$ and Z represents $RED_1$ and Y and Z alternate in their sequence With particular preference, the electrochromic system of the invention comprises at least one electrochromic substance of the formula

 (Ia),

 (Ib),

 (Ic), or

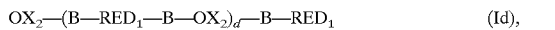 (Id), in which
- $OX_2$, $RED_1$ and B have the meaning indicated above and
- d represents an integer from 1 to 5, and at least one UV absorber selected from the classes of the unsubstituted and substituted cinnamic esters and of the unsubstituted and substituted 2-hydroxybenzophenones.

With very particular preference, the electrochromic solution of the invention comprises at least one electrochromic substance of the formulae (Ia)-(Id) in which
- $OX_2$ represents the radical of a cathodically reducible substance which in its cyclic voltammogram, recorded in an inert solvent at room temperature, exhibits at least two chemically reversible reduction waves, the first of these reduction waves leading to an increase in the absorbance at at least one wavelength in the visible region of the electromagnetic spectrum,
- $RED_1$ represents the radical of an anodically reversibly oxidizable substance which in its cyclic voltammogram, recorded in an inert solvent at room temperature, exhibits at least two chemically reversible oxidation waves, the first of these oxidation waves leading to an increase in the absorbance at at least one wavelength in the visible region of the electromagnetic spectrum, and
- B represents a bridge, and at least one UV absorber selected from the classes of the unsubstituted and substituted cinnamic esters, preferably of the unsubstituted and substituted 3,3-diphenylacrylic esters and of the unsubstituted and substituted 2-cyano-3,3-diphenylacrylic esters, and from the class of the unsubstituted and substituted 2-hydroxybenzophenones.

Particular preference is given to an electrochromic solution of the invention which comprises at least one substance of the formula (Ia)-(Id) in which $OX_2$ represents a radical of the formulae

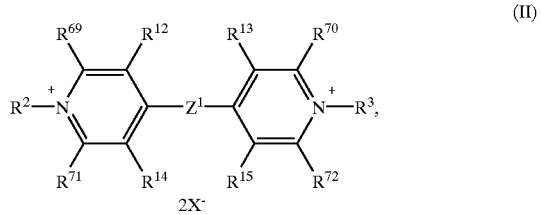 (II)

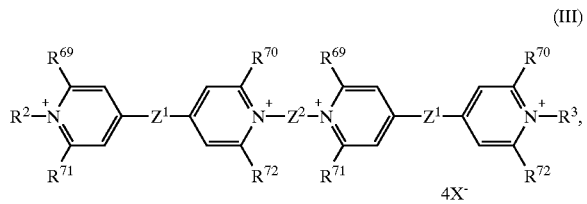 (III)

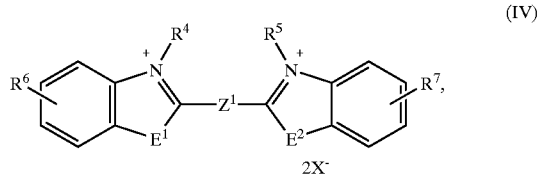 (IV)

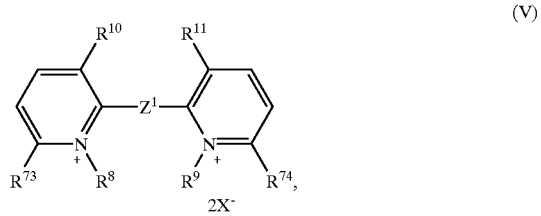 (V)

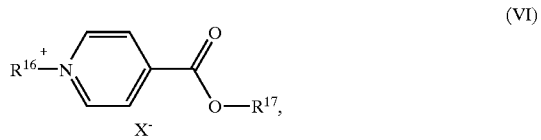 (VI)

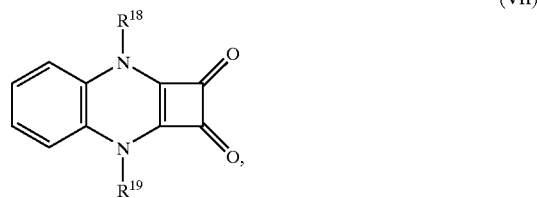 (VII)

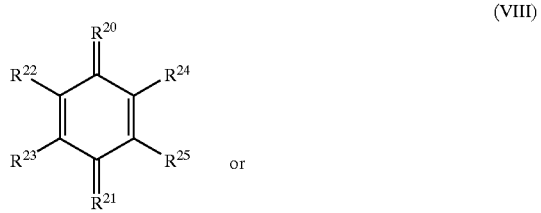 (VIII)

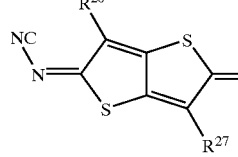 or

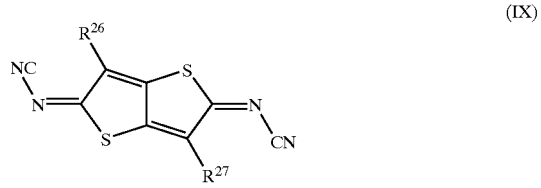 (IX)

where

R$^2$ to R$^5$, R$^8$, R$^9$, R$^{16}$ to R$^{19}$ independently of one another denote C$_1$- to C$_{18}$-alkyl, C$_2$- to C$_{12}$-alkenyl, C$_3$- to C$_7$-cycloalkyl, C$_7$- to C$_{15}$-aralkyl or C$_6$- to C$_{10}$-aryl, or R$^4$ and R$^5$ or R$^8$ and R$^9$ together form a —(CH$_2$)$_2$— or —(CH$_2$)$_3$— bridge, R$^6$, R$^7$ and R$^{22}$ to R$^{25}$ independently of one another denote hydrogen, C$_1$- to C$_4$-alkyl, C$_1$- to C$_4$-alkoxy, halogen, cyano, nitro or C$_1$- to C$_4$-alkoxycarbonyl, or R$^{22}$ and R$^{23}$ and/or R$^{24}$ and R$^{25}$ form a —CH=CH—CH=OH— bridge, R$^{10}$ and R$^{11}$; R$^{12}$ and R$^{13}$; R$^{14}$ and R$^{15}$ independently of one another denote hydrogen or in pairs denote a —(CH$_2$)$_2$—, —(CH$_2$)$_3$— or —CH=CH— bridge, R$^{20}$ and R$^{21}$ independently of one another denote O, N—CN, C(CN)$_2$ or N—C$_6$- to C$_{10}$-aryl, R$^{26}$ denotes hydrogen, C$_1$- to C$_4$-alkyl, C$_1$- to C$_4$-alkoxy, halogen, cyano, nitro, C$_1$- to C$_4$-alkoxycarbonyl or C$_6$- to C$_{10}$-aryl, R$^{69}$ to R$^{74}$ independently of one another denote hydrogen or C$_1$–C$_6$-alkyl, or R$^{69}$; R$^{12}$ and/or R$^{70}$; R$^{13}$ form a —CH=CH—CH=CH— bridge, E$^1$ and E$^2$ independently of one another denote O, S, NR$^1$ or C(CH$_3$)$_2$, or E$^1$ and E$^2$ together form an —N—(CH$_2$)$_2$—N— bridge, R$^1$ denotes C$_1$- to C$_{18}$-alkyl, C$_2$- to C$_{12}$-alkenyl, C$_4$- to C$_7$-cycloalkyl, C$_7$- to C$_{15}$-aralkyl, C$_6$- to C$_{10}$-aryl, Z$^1$ denotes a direct bond, —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)$_3$)=N—N=C(CH$_3$)— or —CCl=N—N=CCl—, Z$^2$ denotes —(CH$_2$)$_r$— or —CH$_2$—C$_6$H$_4$—CH$_2$—, r denotes an integer from 1 to 10, X$^-$ denotes an anion which is redox-inert under the conditions, where the bond to the bridge B is via one of the radicals R$^2$-R$^{19}$, R$^{22}$-R$^{27}$ or, if E$^1$ or E$^2$ represents NR$^1$, is via R$^1$, and the radicals mentioned in that case represent a direct bond, RED$_1$ represents one of the following radicals

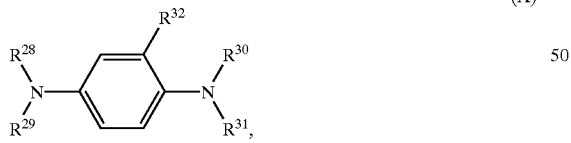

(X)

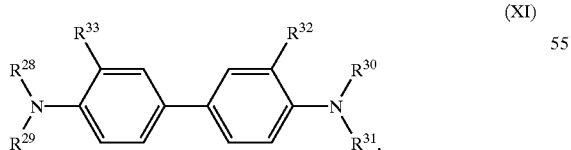

(XI)

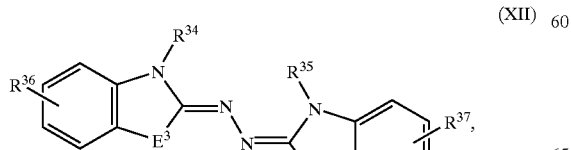

(XII)

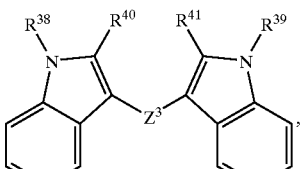

(XIII)

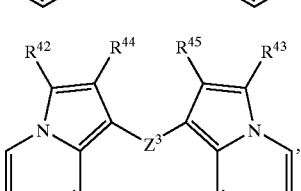

(XIV)

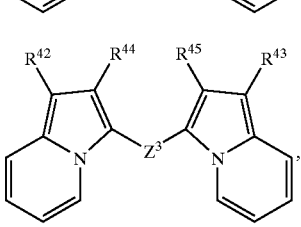

(XV)

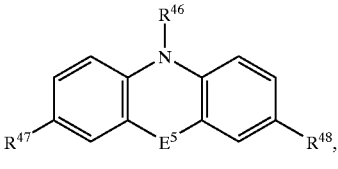

(XVI)

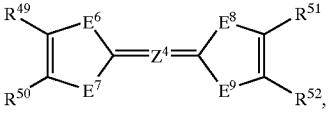

(XVII)

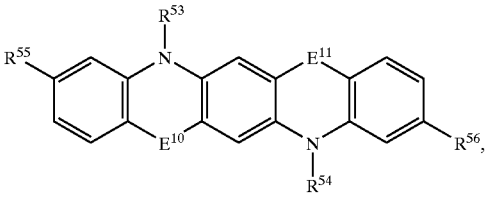

(XVIII)

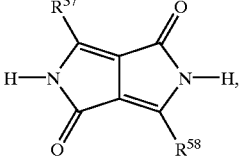

(XIX)

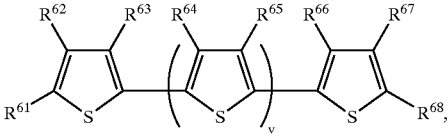

(XX)

in which

R$^{28}$ to R$^{31}$, R$^{34}$, R$^{35}$, R$^{38}$, R$^{39}$, R$^{46}$, R$^{53}$ and R$^{54}$ independently of one another denote C$_1$- to C$_{18}$-alkyl, C$_2$- to C$_{12}$-alkenyl, C$_3$- to C$_7$-cycloalkyl, C$_7$- to C$_{15}$-aralkyl or C$_6$- to C$_{10}$-aryl, and R$^{46}$, R$^{53}$ and R$^{54}$ additionally denote hydrogen, R$^{32}$, R$^{33}$, R$^{36}$, R$^{37}$, R$^{40}$, R$^{41}$, R$^{42}$ to R$^{45}$, R$^{47}$, R$^{48}$, R$^{49}$ to R$^{52}$ and R$^{55}$ to R$^{57}$ independently of one another denote hydrogen, $C_1$- to $C_4$-alkyl, $C_1$- to $C_4$-alkoxy, halogen, cyano, nitro, $C_1$- to $C_4$-alkoxycarbonyl or $C_6$- to $C_{10}$-aryl and $R^{57}$ and $R^{58}$ additionally denote an optionally benzo-fused aromatic or quasiaromatic five- or six-membered heterocyclic ring and $R^{48}$ additionally denotes $NR^{75}R^{76}$, $R^{49}$ and $R^{50}$ and/or $R^{51}$ and $R^{52}$ form a —$(CH_2)_3$—, —$(CH_2)_4$—, —$(CH_2)_5$— or —CH=CH—CH=CH— bridge, $Z^3$ denotes a direct bond, a —CH=CH— or —N=N— bridge, =$Z^4$= denotes a direct double bond, a =CH—CH= or =N—N= bridge, $E^3$ to $E^5$, $E^{10}$ and $E^{11}$ independently of one another denote O, S, $NR^{59}$ or $C(CH_3)_2$, and $E^5$ additionally denotes C=O or $SO_2$, or $E^3$ and $E^4$ independently of one another denote —CH=CH—, $E^6$ to $E^9$ independently of one another denote S, Se or $NR^{59}$, $R^{59}$, $R^{75}$ and $R^{76}$ independently of one another denote $C_1$- to $C_{12}$-alkyl, $C_2$- to $C_8$-alkenyl, $C_3$- to $C_7$-cycloalkyl, $C_7$- to $C_{15}$-aralkyl or $C_6$- to $C_{10}$-aryl, and $R^{75}$ additionally denotes hydrogen, or $R^{75}$ and $R^{76}$ in the definition of $NR^{75}R^{76}$ form, together with the N atom to which they are attached, a five- or six-membered, saturated ring which can contain further heteroatoms, $R^{61}$ to $R^{68}$ independently of one another denote hydrogen, $C_1$- to $C_6$-alkyl, $C_1$- to $C_4$-alkoxy, cyano, $C_1$- to $C_4$-alkoxycarbonyl or $C_6$- to $C_{10}$-aryl, or $R^{61}$ to $R^{62}$ and $R^{67}$; $R^{68}$ independently of one another, together form a —$(CH)_2)_3$—, —$(CH_2)_4$— or —CH=CH—CH=CH— bridge, v denotes an integer between 0 and 10, the bond to the bridge B being via one of the radicals $R^{28}$-$R^{58}$, $R^{61}$, $R^{62}$, $R^{67}$, $R^{68}$ or, if one of the radicals $E^3$-$E^{11}$ represents $NR^{59}$, is via $R^{59}$ and the above-mentioned radicals in that case represent a direct bond, and B represents a bridge of the formula —$(CH_2)_n$— or —$[Y^1_s(CH_2)_m$—$Y^2]_o$—$(CH_2)_p$—$Y^3_q$—, each of which is unsubstituted or substituted by $C_1$- to $C_4$-alkoxy, halogen or phenyl, $Y^1$ to $Y^3$ independently of one another represent O, S, $NR^{60}$, COO, CONH, NHCONH, cyclopentanediyl, cyclohexanediyl, phenylene or naphthylene, $R^{60}$ denotes $C_1$- to $C_6$-alkyl, $C_2$- to $C_6$-alkenyl, $C_4$- to $C_7$-cycloalkyl, $C_7$- to $C_{15}$-aralkyl or $C_6$- to $C_{10}$-aryl, n denotes an integer from 1 to 12, m and p independently of one another denote an integer from 0 to 8, o denotes an integer from 0 to 6, and q and s independently of one another denote 0 or 1, and comprises at least one UV absorber selected from the formulae

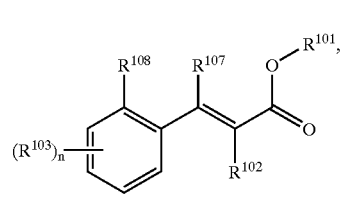

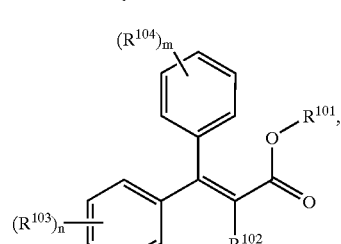

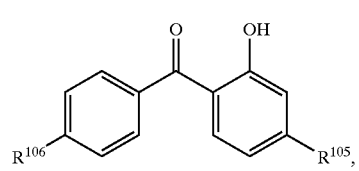

in which
$R^{101}$ represents linear or branched $C_1$- to $C_{20}$-alkyl,
$R^{102}$ represents hydrogen, cyano or $COOR^1$,
$R^{103}$, $R^{104}$ and $R^{106}$ independently of one another represent hydrogen, $C_1$- to $C_{12}$-alkyl or $C_1$- to $C_{12}$-alkoxy,
$R^{105}$ represents hydrogen, $C_1$- to $C_{12}$-alkyl, $C_1$- to $C_{12}$-alkoxy or hydroxyl,
$R^{107}$ represents hydrogen or $C_1$- to $C_{12}$-alkyl,
$R^{108}$ represents hydrogen or
$R^{107}$ together with $R^{108}$ represent a $C_2$- or $C_3$-bridge, which is unsubstituted or substituted by up to 3 $C_1$- to $C_4$-alkyl, and
n and m independently of one another represent an integer between 1 and 3

Very particular preference is given to an electrochromic solution of the invention which comprises at least one substance of the formula (Ia)-(Id)
in which
$OX_2$ represents a radical of the formula (II), (III), (IV) or (V)
where
$R^2$, $R^3$, $R^4$, $R^5$, $R^8$ and $R^9$ independently of one another represent $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl,
$R^6$ and $R^7$ independently of one another represent hydrogen, methyl, ethyl, methoxy, ethoxy, fluoro, chloro, bromo, cyano, nitro, methoxycarbonyl or ethoxycarbonyl,
$R^{10}$, $R^{11}$; $R^{12}$, $R^{13}$ and $R^{14}$, $R^{15}$ independently of one another represent hydrogen or, if $Z^1$ denotes a direct bond, in each case together represent a —$(CH_2)_2$—, —$(CH_2)_3$— or —CH=CH— bridge,
or
$R^4$, $R^5$ and $R^8$, $R^9$ independently of one another in pairs together represent a —$(CH_2)_2$— or —$(CH_2)_3$— bridge if $Z^1$ denotes a direct body,
$R^{69}$ to $R^{74}$ independently of one another denote hydrogen or $C_1$–$C_4$-alkyl,
$E^1$ and $E^2$ are identical and represent O, S, $NR^1$ or $C(CH_3)_2$ or together form an —N—$(CH_2)_2$—N— bridge, $R^1$ represents $C_1$- to $C_{12}$-alkyl, $C_2$- to $C_4$-alkenyl, $C_5$- to $C_7$-cycloalkyl, $C_7$- to $C_{15}$-aralkyl or $C_6$- to $C_{10}$-aryl, $Z^1$ represents a direct bond, —CH=CH—, C(CH$_3$)=CH—, —C(CN)=CH—, —C≡C— or —CH=N—N=CH—, $Z^2$ represents —(CH)$_r$— or —CH$_2$—C$_6$H$_4$—CH$_2$—, r represents an integer between 1 and 6, $X^-$ represents a colourless anion which is redox-inert under the conditions, where the bond to the bridge B is via one of the radicals $R^2$-$R^{11}$ or, if $E^1$ or $E^2$ represents $NR^1$, is via $R^1$, and the abovementioned radicals in that case represent a direct bond, $RED_1$ represents a radical of the formula (X), (XI), (XII), (XIII), (XVI), (XVII), (XVIII) or (XX), where $R^{28}$ to $R^{31}$, $R^{34}$, $R^{35}$, $R^{38}$, $R^{39}$, $R^{46}$, $R^{53}$ and $R^{54}$ independently of one another denote $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl and $R^{46}$, $R^{53}$ and $R^{54}$ additionally denote hydrogen, $R^{32}$, $R^{33}$, $R^{36}$, $R^{37}$, $R^{40}$, $R^{41}$, $R^{47}$ to $R^{52}$, $R^{55}$ and $R^{56}$ independently of one another denote hydrogen, methyl, ethyl, methoxy, ethoxy, fluoro, chloro, bromo, cyano, nitro, methoxycarbonyl, ethoxycarbonyl or phenyl, and $R^{57}$ and $R^{58}$ additionally denote 2- or 4-pyridyl, and $R^{48}$ additionally denotes $NR^{75}R^{76}$, $Z^3$ denotes a direct bond, a —CH=CH— or —N—N— bridge, =$Z^4$= denotes a direct double bond, a =CH—CH= or =N—N= bridge, $E^3$ to $E^5$, $E^{10}$ and $E^{11}$, independently of one another denote O, S, $NR^{59}$ or C(CH$_3$)$_2$, but $E^3$ and $E^4$ have the same meaning, $E^6$ to $E^9$ are identical to one another and denote S, Se or $NR^{59}$, and $E^5$ additionally denotes C=O, $E^6$ represents $NR^{59}$, where $R^{59}$ denotes a direct bond to the bridge B, and $E^7$ to $E^9$ possess the meaning indicated above, but need not be identical to one another, $R^{59}$, $R^{75}$ and $R^{76}$ independently of one another denote $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl, and $R^{75}$ additionally denotes hydrogen, or $R^{75}$ and $R^{76}$ in the definition $NR^{75}R^{76}$ denote, together with the N atom to which they are attached, pyrrolidino, piperidino or morpholino, $R^{61}$, $R^{62}$ and $R^{67}$, $R^{68}$ independently of one another represent hydrogen, $C_1$- to $C_4$-alkyl, methoxycarbonyl, ethoxycarbonyl or phenyl, or in pairs together represent a —(CH$_2$)$_3$— or —(CH$_2$)$_4$— bridge, $R^{63}$ to $R^{66}$ represent hydrogen, and v represents an integer from 1 to 6, where the bond to the bridge B is via one of the radicals $R^{28}$-$R^{41}$, $R^{16}$-$R^{56}$, $R^{61}R^{62}$, $R^{67}$, $R^{68}$ or, if one of the radicals $E^3$-$E^{11}$ represents $NR^{59}$, is via $R^{59}$, and the abovementioned radicals in that case represent a direct bond, B represents a bridge of the formula —(CH$_2$)$_n$—, —(CH$_2$)$_m$—O—(CH$_2$)$_p$—, —(CH)$_m$—NR$^{60}$—(CH$_2$)$_p$—, —(CH$_2$)$_m$—C$_6$H$_4$—(CH$_2$)$_p$—, —[O—(CH$_2$)$_p$]$_o$—O—, —[NR$^{60}$—(CH$_2$)$_p$]$_o$—NR$^{60}$—, —[C$_6$H$_4$—(CH$_2$)$_p$]$_o$—C$_6$H$_4$—, —(CH$_2$)$_m$—OCO—C$_6$H$_4$—COO—(CH$_2$)$_p$—, —(CH$_2$)$_m$—NHCO—C$_6$H$_4$—CONH—

(CH$_2$)$_p$—, —(CH$_2$)$_m$—NHCONH—C$_6$H$_4$—NHCONH—(CH$_2$)$_p$—, —(CH$_2$)$_m$—OCO—(CH$_2$)$_t$—COO—(CH$_2$)—, —(CH$_2$)$_m$—NHCO—(CH$_2$)$_t$—CONH—(CH)$_p$—, —(CH$_2$)$_m$—NHCONH—(CH$_2$)$_t$—NHCONH—(CH$_2$)$_p$—, $R^{60}$ represents methyl, ethyl, benzyl or phenyl, n represents an integer from 1 to 10, m and p independently of one another represent an integer from 0 to 4, o represents an integer from 0 to 2, and t represents an integer from 1 to 6, and at least one UV absorber selected from the formulae (C), (CI) and (CII)

in which $R^{101}$ represents linear or branched $C_1$- to $C_{20}$-alkyl, $R^{102}$ represents hydrogen or cyano, $R^{103}$, $R^{104}$ and $R^{106}$ independently of one another represent hydrogen or $C_1$- to $C_{12}$-alkoxy, $R^{105}$ represents $C_1$- to $C_{12}$-alkoxy or hydroxyl, $R^{107}$ and $R^{108}$ represents hydrogen or $R^{107}$ together with $R^{108}$ represent —(CH$_2$)$_2$—, —(CH$_2$)$_3$— or —CH$_2$—C(CH$_3$)$_2$—, and n and m independently of one another represent 1 or 2.

Special preference is given to an electrochromic solution of the invention which comprises at least one substance of the formula (Ia)-(Id)

in which $OX_2$ represents a radical of the formula (II), (IV) or (V)

in which $R^2$, $R^4$ and $R^8$ represent a direct bond to the bridge B, $R^3$, $R^5$ and $R^9$ independently of one another represent methyl, ethyl, propyl, butyl, pentyl, hexyl, heptyl, octyl, benzyl or phenyl, or in the case of the formula Ic or Id likewise represent a direct bond to the bridge B, $R^6$ and $R^7$ are identical and represent hydrogen, methyl, methoxy, chloro, cyano or methoxycarbonyl, $R^{10}$, $R^{11}$; $R^{12}$, $R^{13}$ and $R^{14}$, $R^{15}$ independently of one another represent hydrogen or, if $Z^1$ denotes a direct bond, represent, in each case in pairs together, a —CH=CH— bridge, $R^{69}$ to $R^{72}$ are identical and denote hydrogen, methyl or ethyl, $R^{73}$ and $R^{74}$ denote hydrogen, $E^1$ and $E^2$ are identical and represent O or S, $Z^1$ represents a direct bond or —CH=CH—, $X^-$ represents a colourless anion which is redox-inert under the conditions, $RED_1$ represents a radical of the formula (X), (XII), (XIII), (XVI) or (XVII), $R^{28}$, $R^{34}$, $R^{38}$, $R^{46}$ and $R^{49}$ represent a direct bond to the bridge B, $R^{29}$ to $R^{31}$, $R^{35}$ and $R^{39}$ independently of one another represent methyl, ethyl, propyl, butyl, pentyl, hexyl, heptyl, octyl, benzyl or phenyl, or, in the case of the formula Ib or Id, $R^{30}$, $R^{35}$ and $R^{39}$ likewise represent the direct bond to the bridge B, $R^{32}$, $R^{47}$ and $R^{48}$ represent hydrogen, $R^{36}$, $R^{37}$, $R^{40}$, $R^{41}$ and $R^{50}$ to $R^{52}$ independently of one another represent hydrogen, methyl, methoxy, chloro, cyano, methoxycarbonyl or phenyl, or, in the case of the formula Ib or Id, $R^{51}$ likewise represents a direct bond to the bridge B, $Z^3$ represents a direct bond, a —CH=CH— or —N=N— bridge, =$Z^4$= represents a direct double bond, a =CH—CH= or =N—N= bridge, $E^3$ to $E^5$ independently of one another represent O, S or $NR^{59}$, but $E^3$ and $E^4$ have the same meaning, $E^6$ to $E^9$ are identical to one another and represent S, Se or $NR^{59}$, $R^{59}$ represents methyl, ethyl, propyl, butyl, pentyl, hexyl, heptyl, octyl, benzyl or phenyl, or, in the case of the formula XVI in Ib or Id, likewise represents a direct bond to the bridge B, B represents a bridge of the formula —$(CH_2)_n$—, —$(CH_2)_m$—O—$(CH_2)_p$—, —$(CH_2)_m$—$NR^{60}$—$(CH_2)_p$—, —$(CH_2)_m$—$C_6H_4$—$(CH_2)_p$—, —O—$(CH_2)_p$—O—, —$NR^{60}$—$(CH_2)_p$—$NR^{60}$—, —$(CH_2)_m$—OCO—$C_6H_4$—COO—$(CH_2)_p$—, —$(CH_2)_m$—NHCO—$C_6H_4$—CONH—$(CH_2)_p$—, —$(CH_2)_m$—NHCONH—$C_6H_4$—NHCONH—$(CH_2)_p$—, —$(CH_2)_m$—OCO—$(CH_2)_t$—COO—$(CH_2)_p$—, —$(CH_2)_m$—NHCO—$(CH_2)_t$—CONH—$(CH_2)_p$—, —$(CH_2)_m$—NHCONH—$(CH_2)_t$—NHCONH—$(CH_2)_p$—, $R^{60}$ represents methyl, n represents an integer from 1 to 10, m and p are identical and represent an integer from 0 to 2, and t represents an integer from 1 to 6, and at least one UV absorber selected from the formulae (C), (CI) and (CII)

in which $R^{101}$ represents methyl, ethyl, 1- or 2-propyl, 1- or 2-butyl, 1-hexyl, 2-ethyl-1-hexyl, 1-octyl or 1-dodecyl, $R^{102}$ represents hydrogen or cyano, $R^{103}$, $R^{104}$ and $R^{106}$ independently of one another represent hydrogen, methoxy, ethoxy, propoxy, butoxy, hexoxy or octoxy, and $R^{105}$ represents methoxy, ethoxy, propoxy, butoxy, hexoxy, octoxy or hydroxyl, $R^{107}$ and $R^{108}$ represent hydrogen or $R^{107}$ together with $R^{108}$ represent —$CH_2$—$C(CH_3)_2$—, and n and m independently of one another represent 1 or 2.

Very particular preference is given to an electrochromic solution of the invention which comprises at least one substance of the formula (Ia) corresponding to one of the formulae

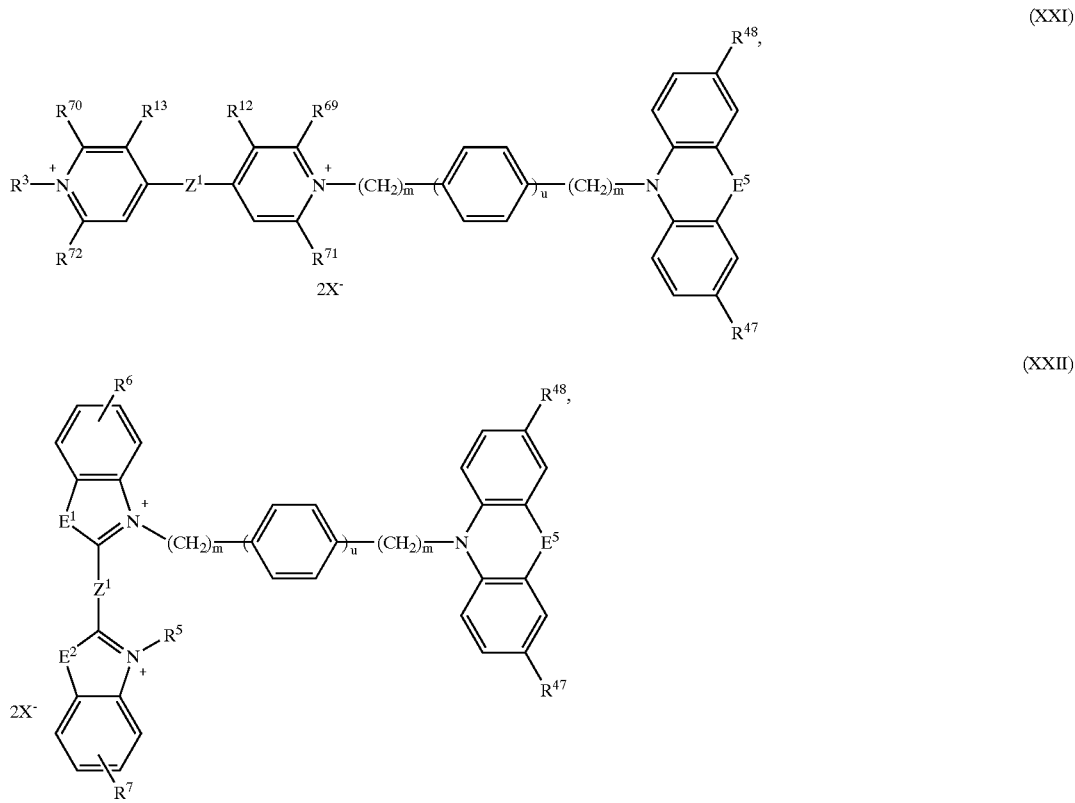

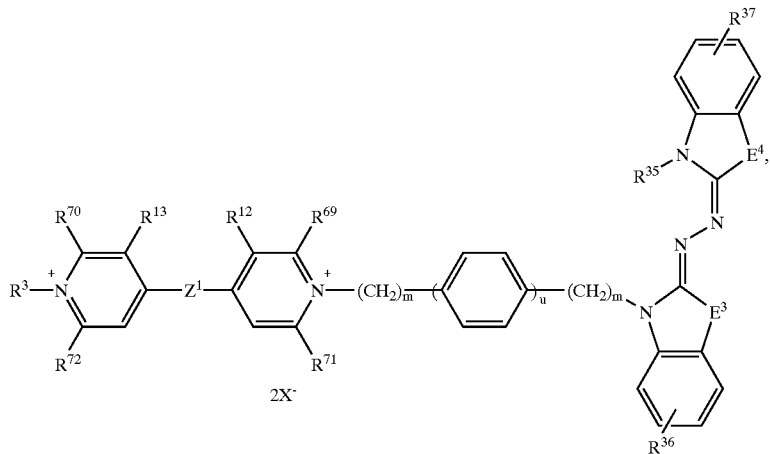
(XXIII)
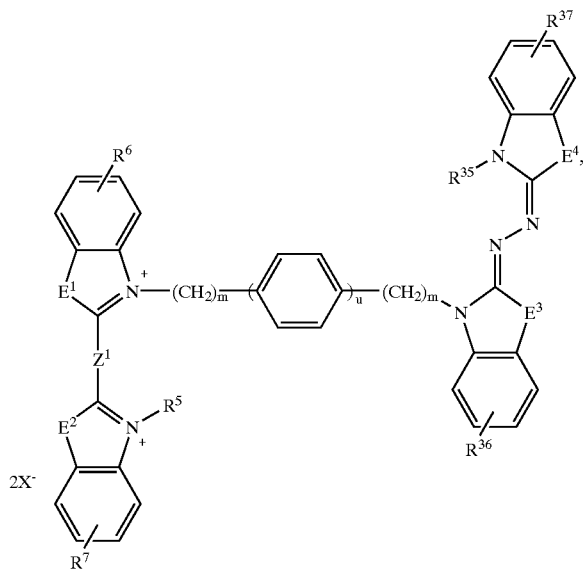
(XXIV)
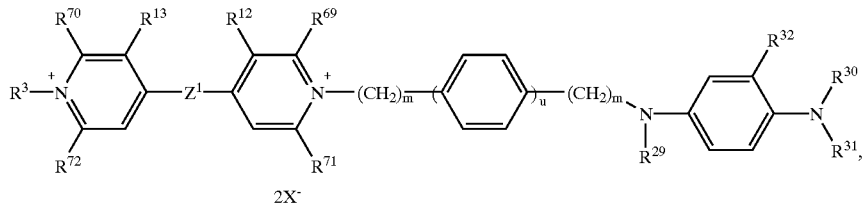
(XXV)

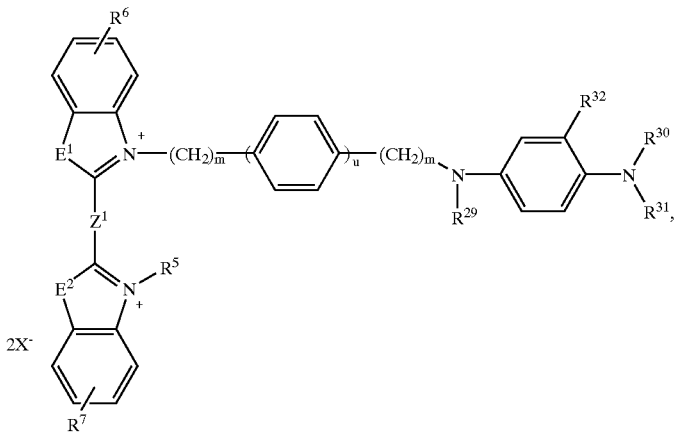
(XXVI)
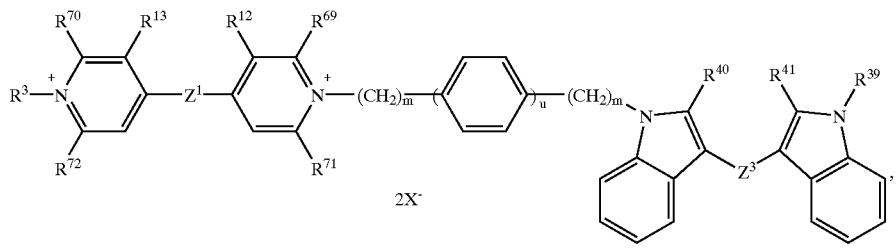
(XXVII)
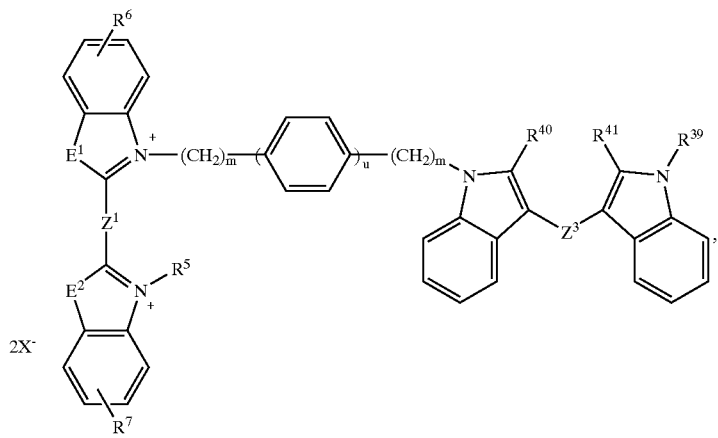
(XXVIII)
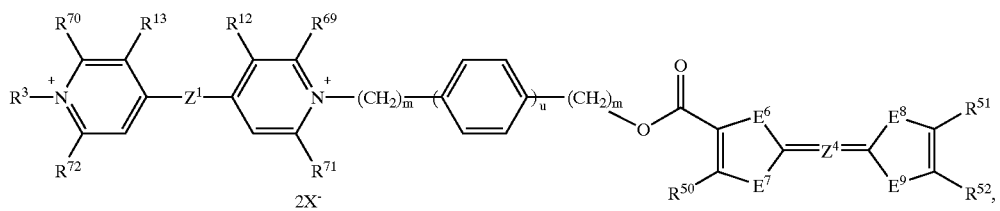
(XXIX)

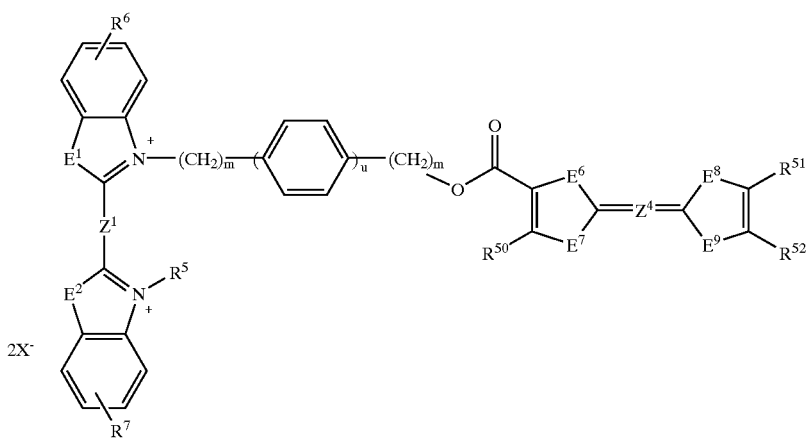
(XXX)
or at least one substance of the formula (Ib) corresponding to one of the formula
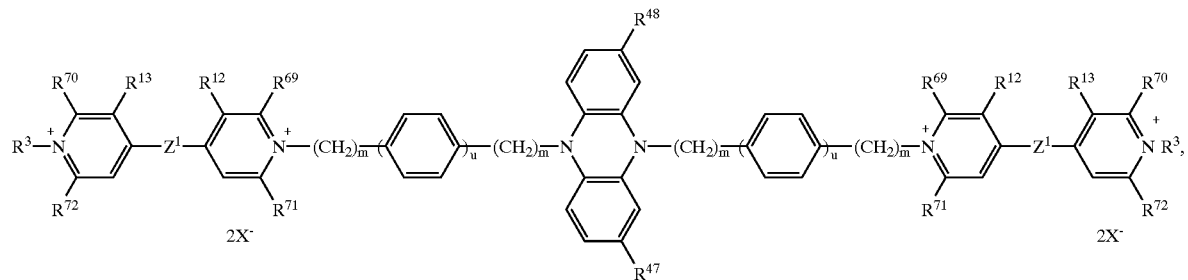
(XXXI)
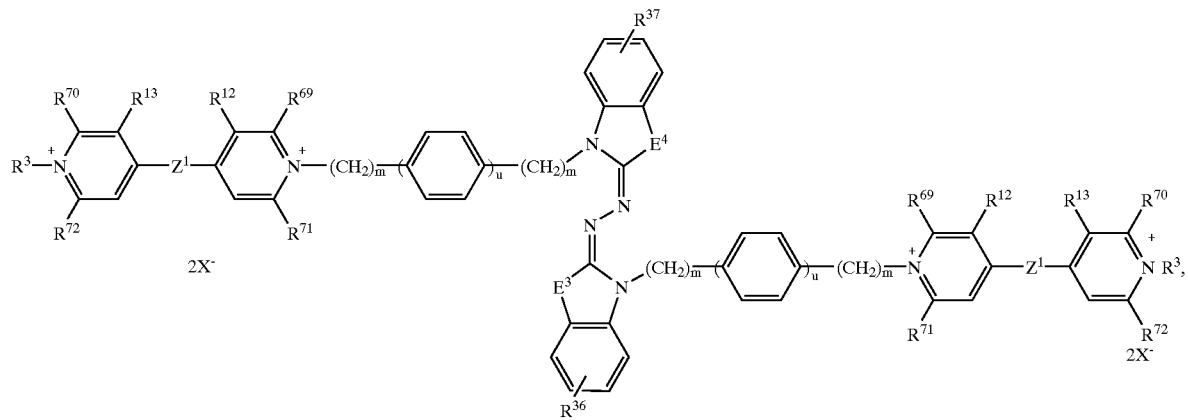
(XXXII)

-continued
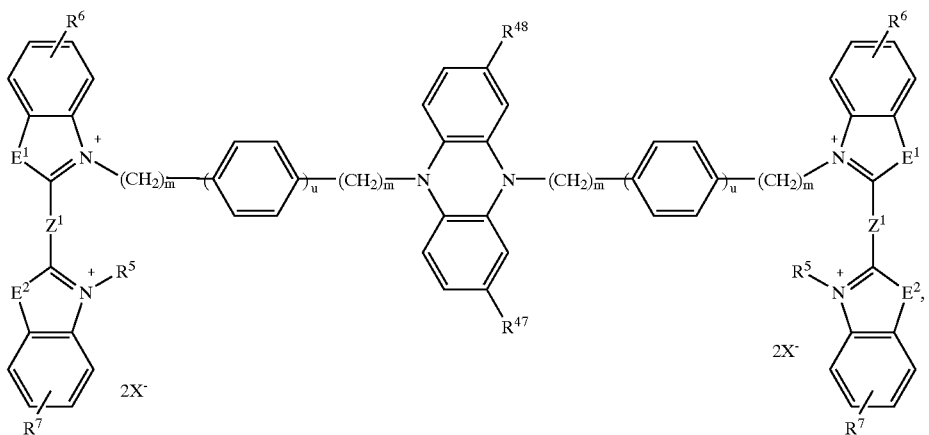
(XXXIII)
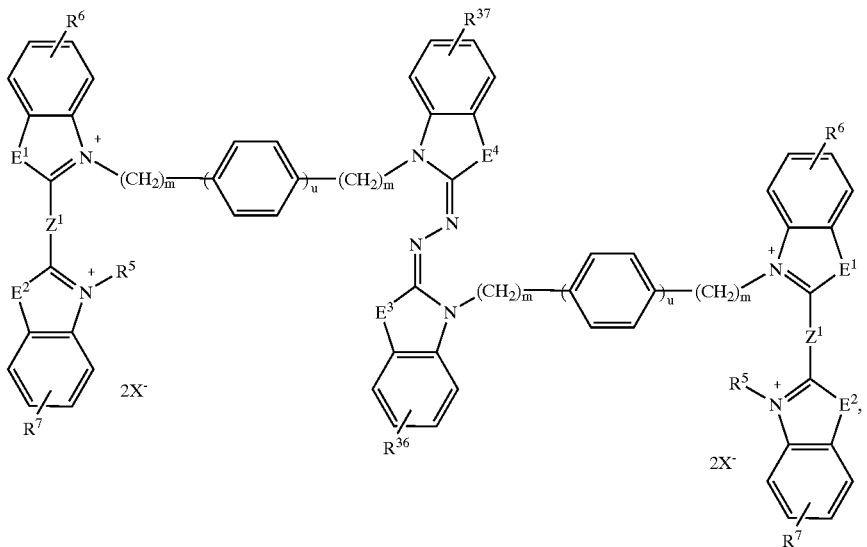
(XXXIV)
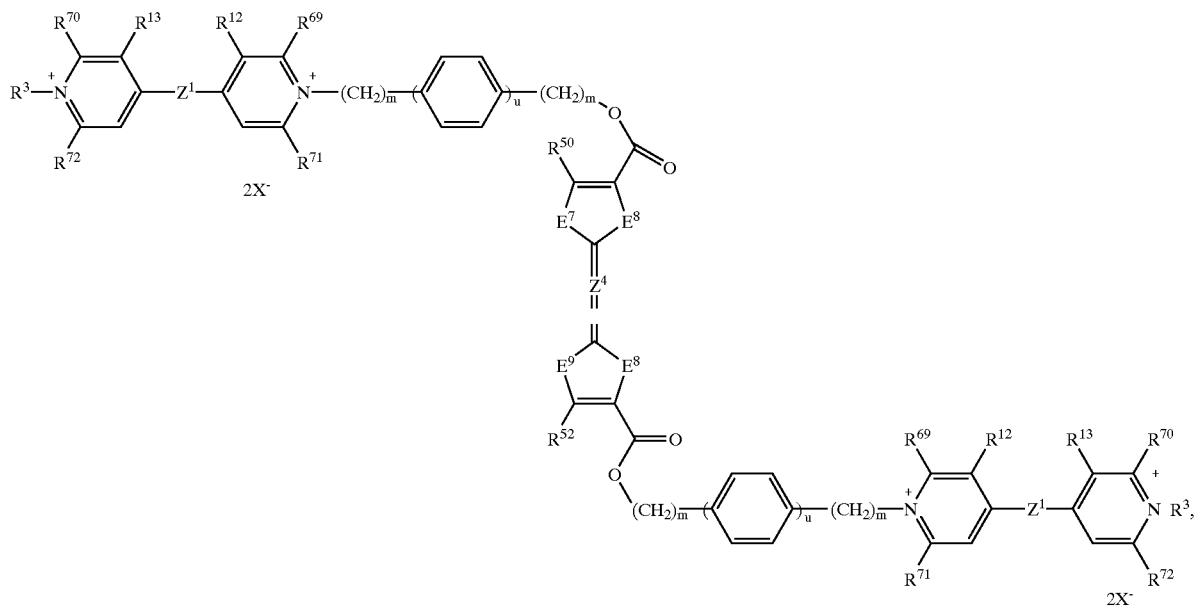
(XXXV)

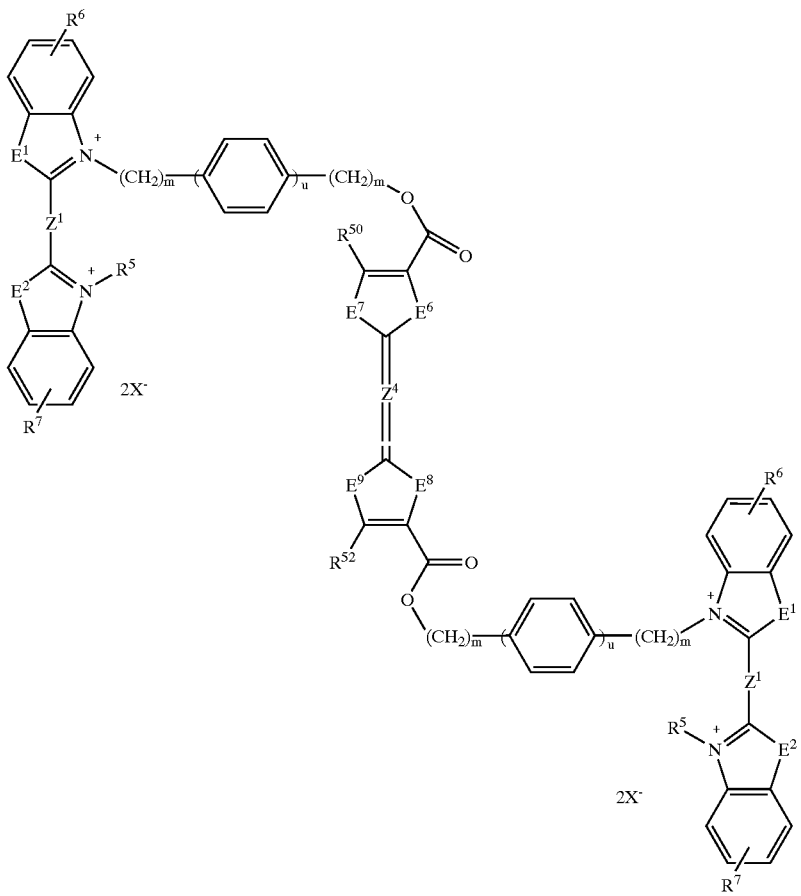
(XXXVI)
or at least one substance of the formula (Ic) corresponding to one of the formulae
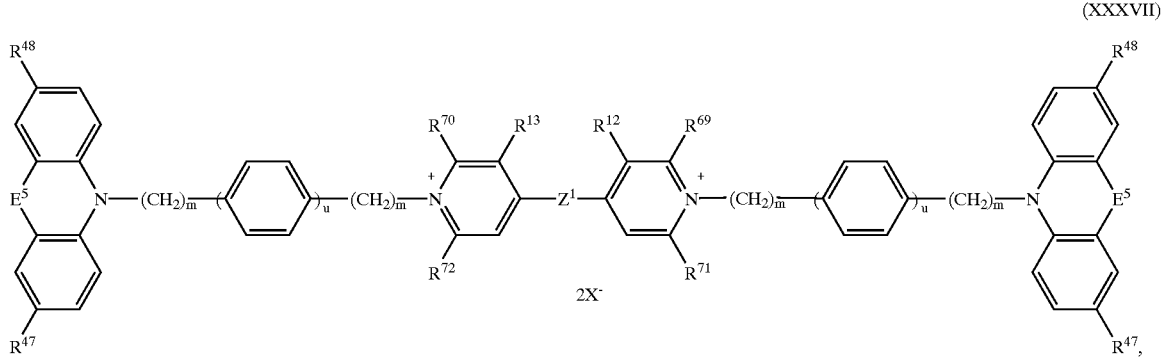
(XXXVII)

-continued
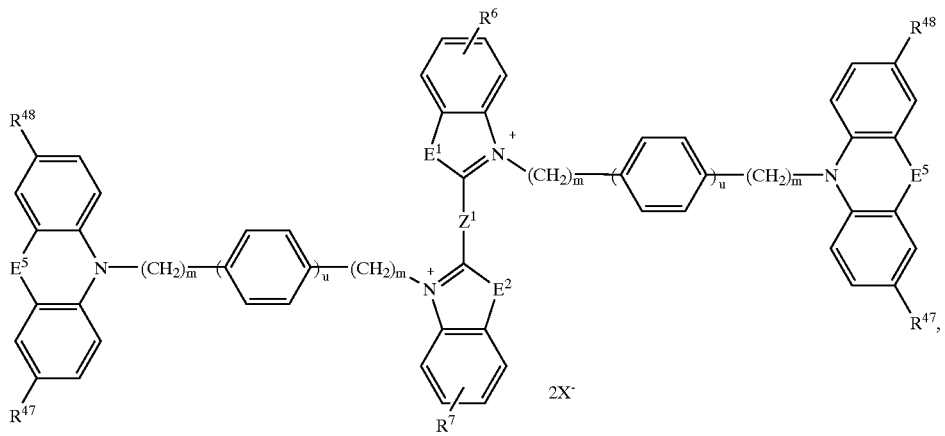
(XXXVIII)
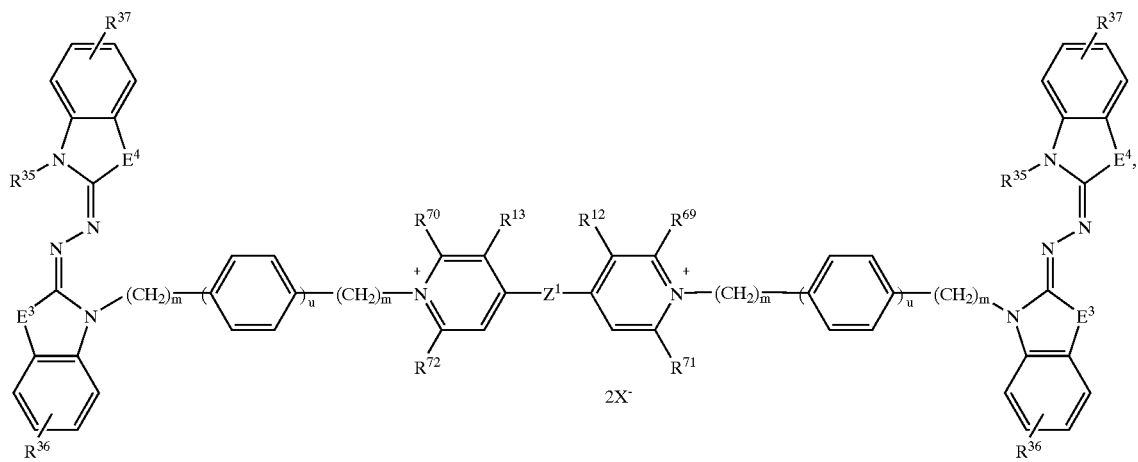
(XXXIX)
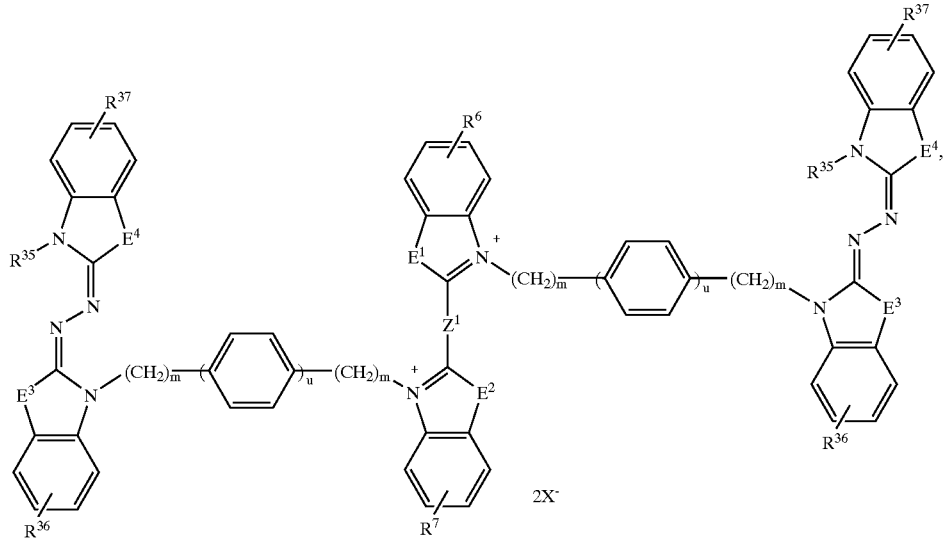
(XL)

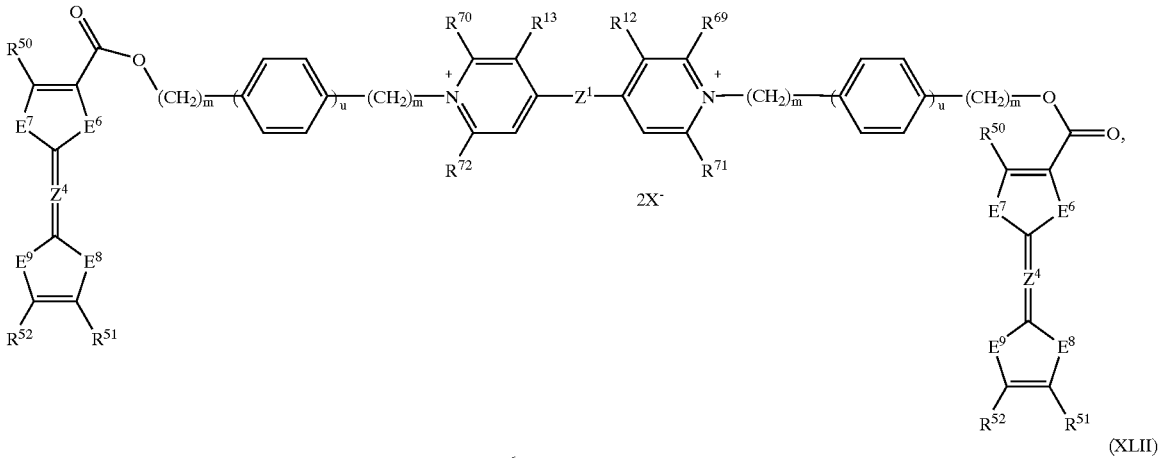

(XLI)

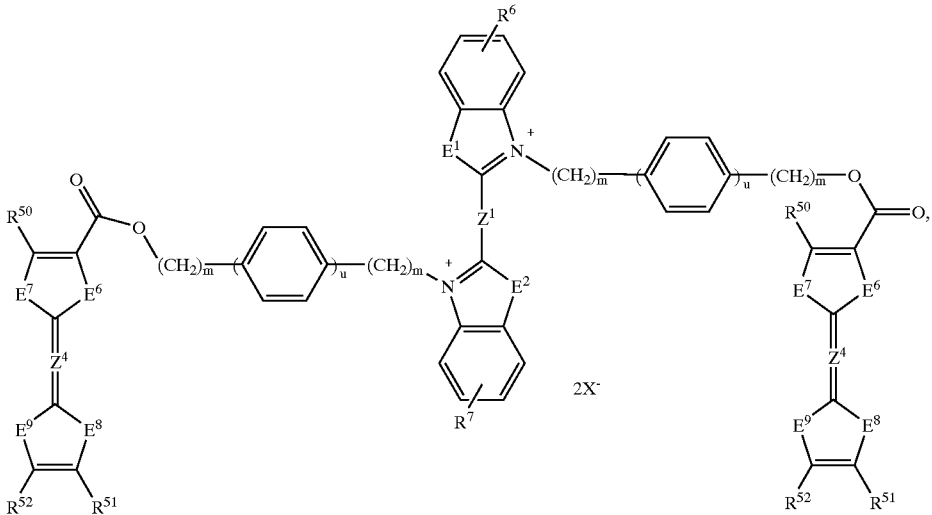

(XLII)

in which
  R³, R⁵, R³⁵ and R³⁹ independently of one another represent methyl, ethyl, propyl, butyl, pentyl, hexyl or benzyl,
  R⁶, R⁷ and R³⁶, R³⁷ in pairs are identical and represent hydrogen, methyl, methoxy, chloro, cyano or methoxycarbonyl,
  R¹² and R¹³ represent hydrogen or, if Z¹ denotes a direct bond, together represent a —CH=CH— bridge,
  R⁶⁹ to R⁷² are identical and represent hydrogen or methyl,
  E¹ and E² are identical and represent O or S,
  Z¹ represents a direct bond or —CH=CH—,
  R³², R⁴⁷ and R⁴⁸ represent hydrogen,
  E³ to E⁵ independently of one another represent O, S or NR⁵⁹, but E³ and E⁴ are identical,
  R²⁹ to R³¹ and R⁵⁹ independently of one another represent methyl, ethyl, propyl, butyl, pentyl, hexyl or benzyl, with R²⁹ to R³¹ preferably being identical,
  R⁴⁰ and R⁴¹ are identical and represent hydrogen, methyl, ethyl, propyl, butyl or phenyl,
  Z³ represents a direct bond, —CH=CH— or —N=N—,
  R⁵⁰ to R⁵² independently of one another represent hydrogen, methyl, methoxy, chloro, cyano, methoxycarbonyl, ethoxycarbonyl or phenyl, but are preferably identical,
  E⁶ to E⁹ are identical to one another and represent S, Se or NR⁵⁹,
  Z⁴ represents a direct double bond, a =CH—CH= or =N—N= bridge,
  m represents an integer from 1 to 5,
  u represents 0 or 1, and
  X⁻ represents a colourless anion which is redox-inert under the conditions,
and a UV absorber of the formula (C)
in which
  R¹⁰¹ represents ethyl or 2-ethyl-1-hexyl,
  R¹⁰² represents hydrogen,
  R¹⁰³ represents ethoxy or methoxy in m- and/or p-position,
  R¹⁰⁷ and R¹⁰⁸ represent hydrogen or
  R¹⁰⁷ together with R¹⁰⁸ represent —CH₂—C(CH₃)₂—, and
  n and m independently of one another represent 1 or 2,
or a UV absorber of the formula (CI)
in which
  R¹⁰¹ represents ethyl or 2-ethyl-1-hexyl,
  R¹⁰² represents cyano, and
  R¹⁰³ and R¹⁰⁴ represent hydrogen and
  n and m represent 1, or a UV absorber of the formula (CII)
in which
R$^{105}$ represents methoxy, ethoxy, octoxy or hydroxyl, and
R$^{106}$ represents hydrogen,
or a mixture of the UV absorbers of the formulae (C) and (CI) or a mixture of the UV absorbers (C) and (CII) or a mixture of the UV absorbers (CI) and (CII) or a mixture of the UV absorbers (C) and (CI) and (CII),
in which the radicals posses the meaning indicated above.

Very particular preference is given to an electrochromic solution of the invention which comprises a UV absorber of the formula (CIII)

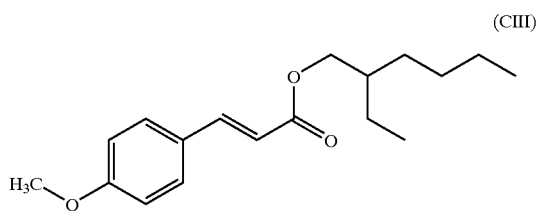

or a UV absorber of the formula (CIIIa)

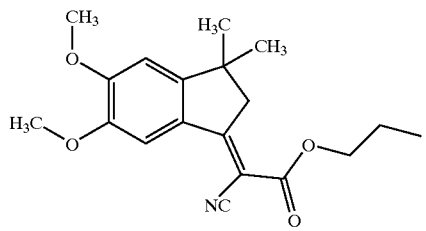

or a UV absorber of the formula (CIV)

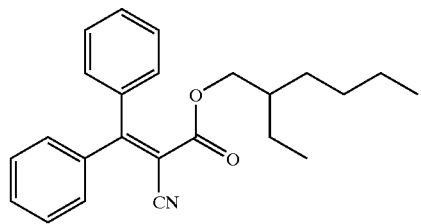

or a UV absorber of the formula (CV)

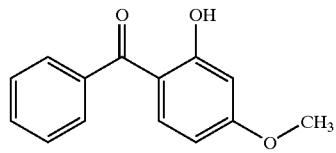

or a mixture of the UV absorbers of the formulae (CIII) and (CIV) or a mixture of the UV absorbers of the formulae (CIV) and (CV) or a mixture of the UV absorbers of the formulae (CIII) and (CV) or a mixture of the UV absorbeer of the formulae (CIIIa) and (CIV) or a mixture of the UV absorber of the formulae (CIIIa) and (CV).

The substances of the formula (I) are known from WO 97/30134.

In the abovementioned definitions of substituents alkyl radicals, including modified versions such a alkoxy or aralkyl radicals, for example, are preferably those having 1 to 12 C atoms, especially having 1 to 8 C atoms, unless indicated otherwise. They can be straight-chain or branched and can if desired carry further substituents such as, for example, $C_1$- to $C_4$-alkoxy, fluoro, chloro, hydroxyl, cyano, $C_1$- to $C_4$-alkoxycarbonyl or COOH.

Cycloalkyl radicals are preferably those having 3 to 7 C atoms, especially 5 or 6 C atoms.

Alkenyl radicals are preferably those having 2 to 8 C atoms, especially 2 to 4 C atoms.

Aryl radicals, including those in aralkyl radicals, are preferably phenyl or naphthyl radicals, especially phenyl radicals. They can be substituted by 1 to 3 of the following radicals: $C_1$- to $C_6$-alkyl, $C_1$- to $C_6$-alkoxy, fluoro, chloro, bromo, cyano, hydroxyl, $C_1$- to $C_6$-alkoxycarbonyl or nitro. Two adjacent radicals can also form a ring.

The electrochromic solution of the invention comprises at least one solvent. Suitable solvents are all solvents which are redox-inert at the chosen voltages and which cannot give off electrophiles or nucleophiles or themselves react as sufficiently strong electrophiles or nucleophiles and so could react with the coloured ionic free radicals. Examples are propylene carbonate, γ-butyrolactone, acetonitrile, propionitrile, glutaronitrile, methylglutaronitrile, 3,3'-oxydipropionitrile, hydroxypropionitrile, dimethylformamide, N-methylpyrrolidone, sulpholane, 3-methylsulpholane or mixtures thereof. Preference is given to propylene carbonate and to mixtures thereof with glutaronitrile or 3-methylsulpholane.

The electrochromic solution of the invention can include at least one inert conductive salt.

Suitable inert conductive salts are lithium, sodium and tetraalkylammonium salts, especially the latter. The alkyl groups can have between 1 and 18 C atoms and can be identical or different. Tetrabutylammonium is preferred Suitable anions for these salts, and also those anions X$^-$ in the formulae (I), (II), (IV), (VI) and (VII) are all colourless anions which are redox-inert. Examples are tetrafluoroborate, tetraphenylborate, cyano-triphenylborate, perchlorate, chloride, nitrate, sulphate, phosphate, methanesulphonate, ethanesulphonate, tetradecanesulphonate, pentadecanesulphonate, trifluoromethanesulphonate, perfluorobutanesulphonate, perfluorooctanesulphonate, benzenesulphonate, chlorobenzenesulphonate, toluenesulphonate, butylbenzenesulphonate, tert-butylbenzenesulphonate, dodecylbenzenesulphonate, naphthalenesulphonate, biphenylsulphonate, benzenedisulphonate, naphthalenedisulphonate, biphenyldisulphonate, nitrobenzenesulphonate, dichlorobenzenesulphonate, trifluoromethylbenzenesulphonate, hexafluorophosphate, hexafluoroarsenate, hexafluorosilicate, 7,8- or 7,9-dicarbanidoundecaborate(1-) or (2-), each of which is unsubstituted or substituted on the B and/or C atoms by one or two methyl, ethyl, butyl or phenyl groups, and also dodecahydrodicarbadodecaborate(2-) or B-methyl-C-phenyldodecahydro-dicarbadodecaborate(1-). In the case of polyvalent anions X⁻ represents one equivalent of this anion, e.g. ½ $SiF_6^{2-}$.

Preferred anions are tetrafluoroborate, pentadecanesulphonate, dodecylbenzenesulphonate, cyanotriphenylborate and 7,8-dicarba-nido-undecaborate(1-)

The conductive slats are preferably employed in the range from 0 to 1 molar.

Further possible additives to the electrochromic solution are thickeners, in order to control the viscosity of the fluid. This can be important for avoiding segregation, i.e. the formation of stripey or spotty coloration on prolonged operation of an electrochromic device comprising the electrochromic fluid of the invention, in the switched-on state, and for controlling the rate of fade after switching off the current.

Suitable thickeners are all compounds usual for these purposes, such as polyacrylate, polymethacrylate (Luctite L®), polycarbonate and polyurethane, for example.

The electrochromic solution can also be in gel form.

A constituent of the electrochromic solution of the invention comprises, in accordance with the invention, UV absorbers. They are employed in the range from 0.01 to 2 mol/l, preferably from 0.04 to 1 mol/l. The UV absorbers present in the solution of the invention are known in principle or can be prepared in analogy to the preparation of known UV absorbers. Preferred UV absorbers are those of the formulae (CIII) (e.g. UVINUL® 3088, BASF), (CIV) (e.g. UVINUL® 3039, BASF) and (CV) (e.g. CHIMASSORB®90, Ciba). These products are highly soluble in the stated solvents: for example, at least 0.8 molar in propylene carbonate.

The action of the UV absorber was measured in electrochromic cells as described below. The exposure apparatus used was the Xenotest 150 S from Heraeus. The output was 1570 W/m² in the "outdoor sunlight" configuration.

It was found, surprisingly, that mixtures of these UV absorbers are considerably more effective than the individual substances. For example, a mixture of the UV absorbers of the formulae (CIV) and (CV) in concentrations of 0.05 molar each is just as effective as the UV absorber of the formula (CIV) alone in a concentration of 0.4 molar.

The electrochromic solution of the invention comprises the substances of the formula (I), especially of the formulae (Ia) to (Id), in each case in a concentration of at least $10^{-4}$ mol/l, preferably from 0.001 to 1 mol/l. It is also possible to employ mixtures of two or more electrochromic substances of the formula (I)

The electrochromic solutions of the invention are eminently suitable as a constituent of an electrochromic device. In an electrochromic device the electrochromic solution of the invention serves as variable-transmission medium, in other words, under the influence of an electrical voltage the light transmittance of the solution changes, and it passes from a colourless to a coloured state. A further subject of the present invention, accordingly, are electrochromic devices comprising an electrochromic solution of the invention. The design of an electrochromic device, which may be configured, for example, as a window pane, car sunroof, car rearview mirror or display, is known in principle. The electrochromic device of the invention consists of two facing, transparent glass or plastic plates of which one may be mirrored and whose facing sides carry an electroconductive coating of, for example, indium tin oxide (ITO) and between which there is located the electrochromic fluid of the invention. Other suitable conductive materials are antimony-doped tin oxide, fluorine-doped tin oxide, antimony-doped zinc oxide, aluminium-doped zinc oxide, tin oxide, and also conductive organic polymers, such as unsubstituted or substituted polythienyls, polypyrroles, polyanilines, polyacetylene. If one of the plates is mirrored, it can also be used as a conductive layer. The distance between the two plates is generally 0.005–2 mm, preferably 0.02–0.5 mm. The desired distance between the plates is generally established by means of a sealing ring.

Such cells were also used to determine the action of the UV absorbers (see above).

In the case where the electrochromic device is an electrochromic display device, at least one of the two conductive layers, or both, are subdivided into electrically separate segments that are contacted individually.

Alternatively, it is possible for only one of the two plates to carry the conductive coating and to be subdivided into segments. The separation of the segments can be effected, for example, by means of mechanical removal of the conductive layer, for example by scoring, scratching, scraping or milling, or chemically, for example by etching using, for instance, a solution of $FeCl_2$ and $SnCl_2$ in hydrochloric acid This removal of the conductive layer can be locally controlled by means of masks, for example photoresistant masks. Also possible, however, is the production of the electrically separate segments by means of controlled—for example, by means of masks—application—for example, sputtering or printing—of the conductive layer The contacting of the segments takes place, for example, by means of fine strips of conductive material, by means of which the segment is brought into electrically conducting communication with a contact at the edge of the electrochromic device These fine contact strips can consist either of the same material as the conductive layer itself and can be prepared, for example, along with said layer at the same time as it is subdivided into segments as described above. Alternatively, in order to improve the conductivity, they can consist of a different material, such as fine metallic conductors made, for example, from copper or silver. A combination of metallic material and the material of the conductive coating is a further possibility. These metallic conductors may, for example, be applied, e.g. bonded, in fine wire form, or else may be printed on. All of these above-described techniques are common knowledge from the production of liquid-crystal displays (LCD)

The displays can be viewed in transmitted light or else reflectively via mirror coating.

The two plates are laid atop one another with the conductively coated and segmented sides facing, separated by means, for example, of a sealing ring, and are bonded to one another at the edge. The sealing ring may be made, for example, of plastic or thin glass or another material which is inert with respect to the electrochromic fluid. The distance between the plates can also, however, be established by means of different spacers, for example by means of small plastic or glass beads or particular fractions of sand, in which case these spacers are applied together with the adhesive and then together form the sealing ring. The sealing ring includes one or two cutouts which are used to fill the electrochromic device. The distance between the two plates lies between 0.005 and 2 mm, and is preferably from 0.02 to 0.5 mm. In the case of large-surface-area display devices, especially those made of plastic, it may be advantageous to use spacers, for example plastic beads of equal diameter distributed over the area of the display device, to keep the distance between the plates constant.

This display device is filled with an electrochromic fluid via the apertures in the sealing ring, an operation which must be carried out at all times with exclusion of moisture and oxygen. Filling can be carried out, for example, by means of fine cannulas or else by the vacuum filling technique, in which the device and the fluid are placed into a shallow dish and introduced into an evacuable container. This container is evacuated. Then the display device, which includes only one filling aperture, is dipped with said aperture into the fluid. When the vacuum is removed, the fluid is then forced into the display device The self-erasing single-cell electrochromic device of the invention can in addition to the above-described electrochromic substances of the formulae (I), especially of the formulae (Ia) to (Id), also include other such substances, as are described, for example, in U.S. Pat. No. 4,902,108, Topics in Current Chemistry, Vol. 92, pp 1–44 (1980) and Angew. Chem. 90, 927 (1978). Such electrochromic substances hail, for example, from the groups indicated above, under the formulae (II) to (XX), in which case none of the radicals listed is able to possess the definition "direct bond to the bridge B". Examples of other suitable electrochromic co-components are tetrazolinium salts or salts or complexes of metal ions, e.g. $[Fe(C_5H_5)_2]^{0/1+}$. The admixture of such redox systems may, for example, be advantageous in order to correct the colour of the electrochromic device of the invention, for example of the display, in the switched-on state or to render the said colour more intense.

EXAMPLES

Example 1
Preparing an Electrochromic Substance of the Formula (I)
a) 9.2 g of phenazine were suspended in 60 ml of anhydrous tetrahydrofuran under a nitrogen atmosphere. 30.8 ml of 20% strength by weight phenyl-lithium solution in 7.3 cyclohexane/diethyl ether were added dropwise over the course of 15 minutes, during which the temperature was held at max. 35° C. The solution was subsequently stirred at room temperature for 30 minutes.

At 15° C., 30.2 ml of 1,4-dibromobutane were added in one portion. Upon this addition the temperature rose to 38° C. After 6 h at room temperature, 200 ml of water were added and the pH was adjusted to 7.0. The organic phase was separated off, washed three times with 100 ml of water each time and concentrated in vacuo. Finally, excess 1,4-dibromobutane was distilled off under a pressure of 0.2 mbar. The oily reside was dissolved hot in 400 ml of ethanol. The product precipitated on cooling was filtered off with suction, washed with ethanol and hexane and dried. This gave 8.0 g (41% of theory) of a pale yellow powder of the 9,10-dihydrophenazine of the formula

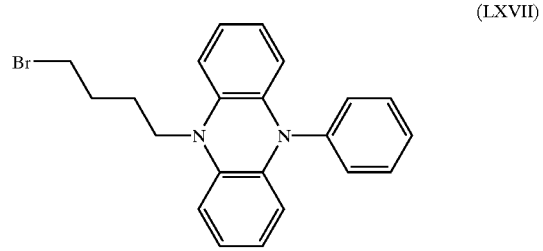

(LXVII)

b) 7.5 g of the 9,10-dihydrophenazine of the formula (LXVII) from a) and 6.1 g of 4,4'-bipyridyl were stirred in 100 ml of acetonitrile at 70° C. under a nitrogen atmosphere for 24 h. After cooling, the mixture was filtered with suction and the solid product washed with 50 ml of acetone. Drying gave 6.3 g (60% of theory) of a salt of the formula

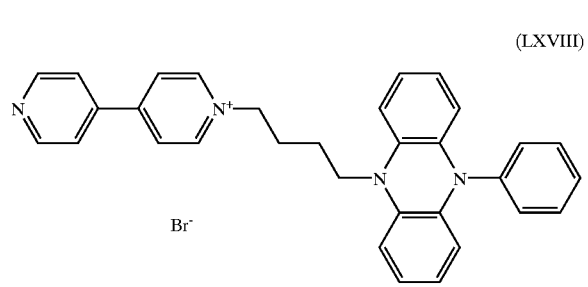

(LXVIII)

c) 6.1 g of the salt obtained in b) were stirred in 70 ml of N-methyl-2-pyrrolidone together with 2.7 ml of benzyl bromide at 70° C. under a nitrogen atmosphere for 7 h. After cooling, the mixture was diluted with 150 ml of toluene and the precipitated product was filtered off with suction. It was washed thoroughly with 150 ml of toluene and 500 ml of hexane and dried. This gave 5.5 g (69% of theory) of the dipyridinium salt of the formula

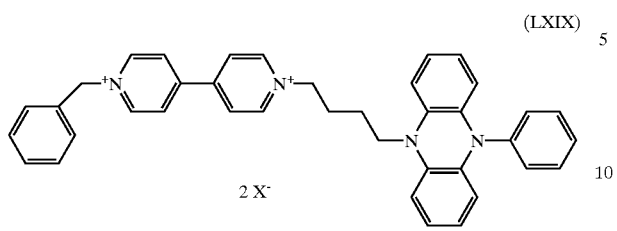

(LXIX)

2 X⁻ where $X^- = Br^-$.

d) 4.0 g of this product from c) were dissolved at 65° C. in 100 ml of methanol under a nitrogen atmosphere 7.4 g of tetrabutylammonium tetrafluoroborate were sprinkled in over the course of 5 minutes. Precipitation occurred. After 5 minutes at 65° C. the mixture was cooled and the precipitate was filtered off with suction, washed with 200 ml of methanol and 50 ml of hexane and dried in vacuo. This gave 3.4 g (83% of theory) of a pale beige powder of the formula (LXIX) with $X^- = BF_4^-$.

Example 2

An ITO-coated glass plate (1) was coated in accordance with FIG. 1 with a ring (2) comprising a mixture of a two-component epoxy adhesive, such as KÖRAPOX® 735 from Kömmerling, Pirmasens, and 3% glass beads of diameter 200 μm as spacers, and two filling apertures (3) were taken out of this ring. A second ITO-coated glass plate (4) was placed with its coated side on this line of adhesive. The adhesive was cured at 130° C. for 10 minutes. The assembly was filled, in a glovebox under a nitrogen atmosphere, with a solution which was 0.02 molar in terms of the electrochromic compound of the formula (LXIX) with $X^- = BF_4^-$ in accordance with Example 1 and 0.4 molar in terms of UV absorber of formula (CIV), in anhydrous, oxygen-free propylene carbonate. The filling apertures (3) were sealed with a hot melt adhesive gun "Pattex Supermatic" from Henkel KGaA, Düsseldorf. This adhesive seal was then coated with the above-described epoxy adhesive for mechanical strengthening, and the assembly was cured at room temperature overnight.

The solution in the cell was virtually colourless. On application of a voltage of 0.9 V the solution turned an intense greenish blue colour, with maxima at 466 and 607 nm. After switching off the supply of current and short-circuiting the cell the contents decoloured again with 10 s.

The absorption curves in the off and on (0.9 V) switching state were measured from 300 to 800 nm in a Cary 4G spectrometer from Varian.

The cell in the switched-off state was then exposed to light in a Xenotest 150 S from Heraeus. The output was 1570 W/m² in the "outdoor sunlight" configuration. After 7 days (168 h) in each case the ell was taken out. The rate ("kinetics") for the colouration and decolouration process, and the spectra, were measured as described above in the off and on state. The spectra in the switched-off state were used to construct different spectra "after exposure"—"before exposure", and these different spectra were assessed.

After 28 days the spectra were virtually unchanged (FIG. 2)

Example 3 (Comparative Example)

A cell was constructed as described in Example 2 but without the UV absorber of the formula (CIV).

The absorption measurements and exposure to light were carried out as in Example 2. After just 7 days a significant increase in the absorption at about 470 nm and a slight increase at about 665 and 735 nm were observed (FIG. 3)

The procedure adopted in Examples 4 to 21 was similar to that in Example 2 However, the UV absorbers and their concentrations were changed. Assessment was carried out using the difference spectra "after exposure"—"before exposure". Assessment was made in accordance with the following ratings:

| | |
|---|---|
| ++ | no change |
| + | slight change |
| 0 | moderate change |
| − | distinct change |
| −− | severe change, but cell still functional |
| empty fields: no measurement | |

| Example | UV absorber | Conc. mol/l | 7 days | 14 days | 21 days | 28 days | 36 days |
|---|---|---|---|---|---|---|---|
| 3 | — | — | −−[a] | | | | |
| 4 | (CIV) | 0.1 | + | +[b] | | | |
| 5 | (CIV) | 0.2 | + | + | 0 | 0 | |
| 6 (=Ex. 2) | (CIV) | 0.4 | ++ | ++[c] | ++ | ++ | |
| 7 | (CIV) | 0.6 | ++ | ++ | | | |
| 8 | (CIV) | 0.8 | ++ | ++ | | ++ | + |
| 9 | (CIIIa) | 0.1 | ++ | ++ | | | |
| 10 | (CIII) | 0.2 | − | −− | | | |
| 11 | (CIII) | 0.4 | + | 0 | | | |
| 12 | (CIII) | 0.8 | +[d] | +[d] | | − | |
| 13 | (CII)[e] | 0.1 | −− | | | | |
| 14 | (CV) | 0.1 | 0 | | | | |
| 15 | (CV) | 0.2 | − | | | | |
| 16 | (CV) | 0.4 | ++ | | | | |
| 17 | (CII)[e] (CIII) | 0.1 0.1 | + | 0 | | | |
| 18 | (CIV) (CIII) | 0.4 0.4 | ++ | ++ | | ++ | + |
| 19 | (CV) (CIV) | 0.5 0.05 | ++ | ++[f] | | | |
| 20 | (CV) (CIV) | 0.1 0.1 | ++ | | | | |
| 21 | (CIIIa) (CIV) | 0.07 0.07 | ++ | ++ | | | |

[a] see FIG. 3
[b] see FIG. 4
[c] see FIG. 2
[d] spectrum in the switched-on state is unchanged
[e] $R^{105}$ = octoxy, $R^{106}$ = H
[f] see FIG. 5.

Entirely analogous results were obtained with the electrochromic substances and UV absorbers of Examples 22 to 47.

| Example | OX$_2$-B-RED$_1$ | Colour |
|---|---|---|
| 22 |  2 C$_{15}$H$_{13}$SO$_3^{\ominus}$ | blue-violet |
| 23 |  2 C$_2$B$_9$H$_{12}^{\ominus}$ | green |
| 24 |  2 BF$_4^{\ominus}$ | green |

-continued
| | | |
|---|---|---|
| 25 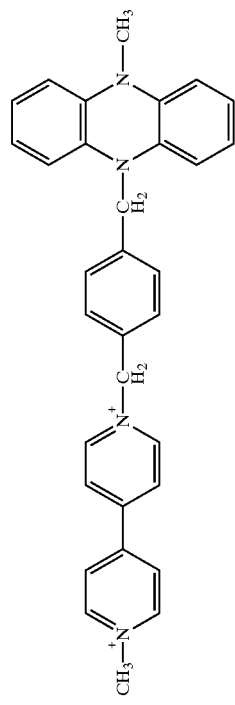 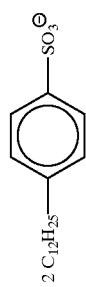 | 26 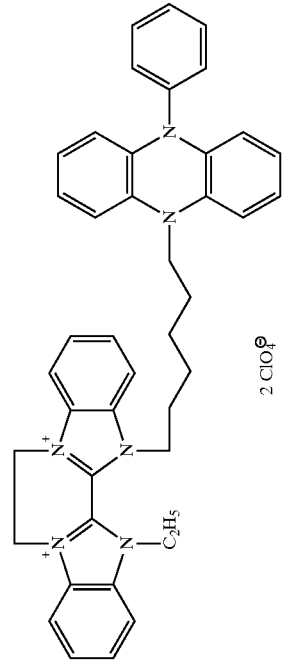 | 27 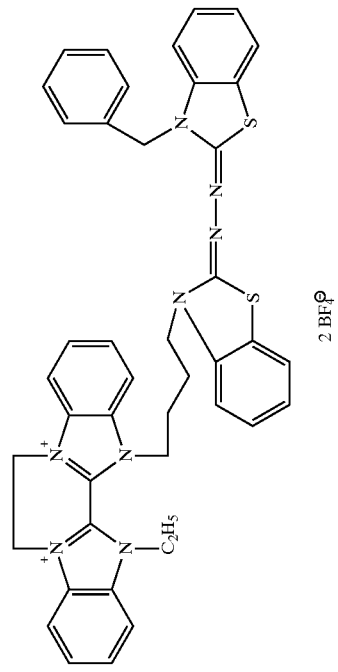 |
| greenish-blue | green | green |

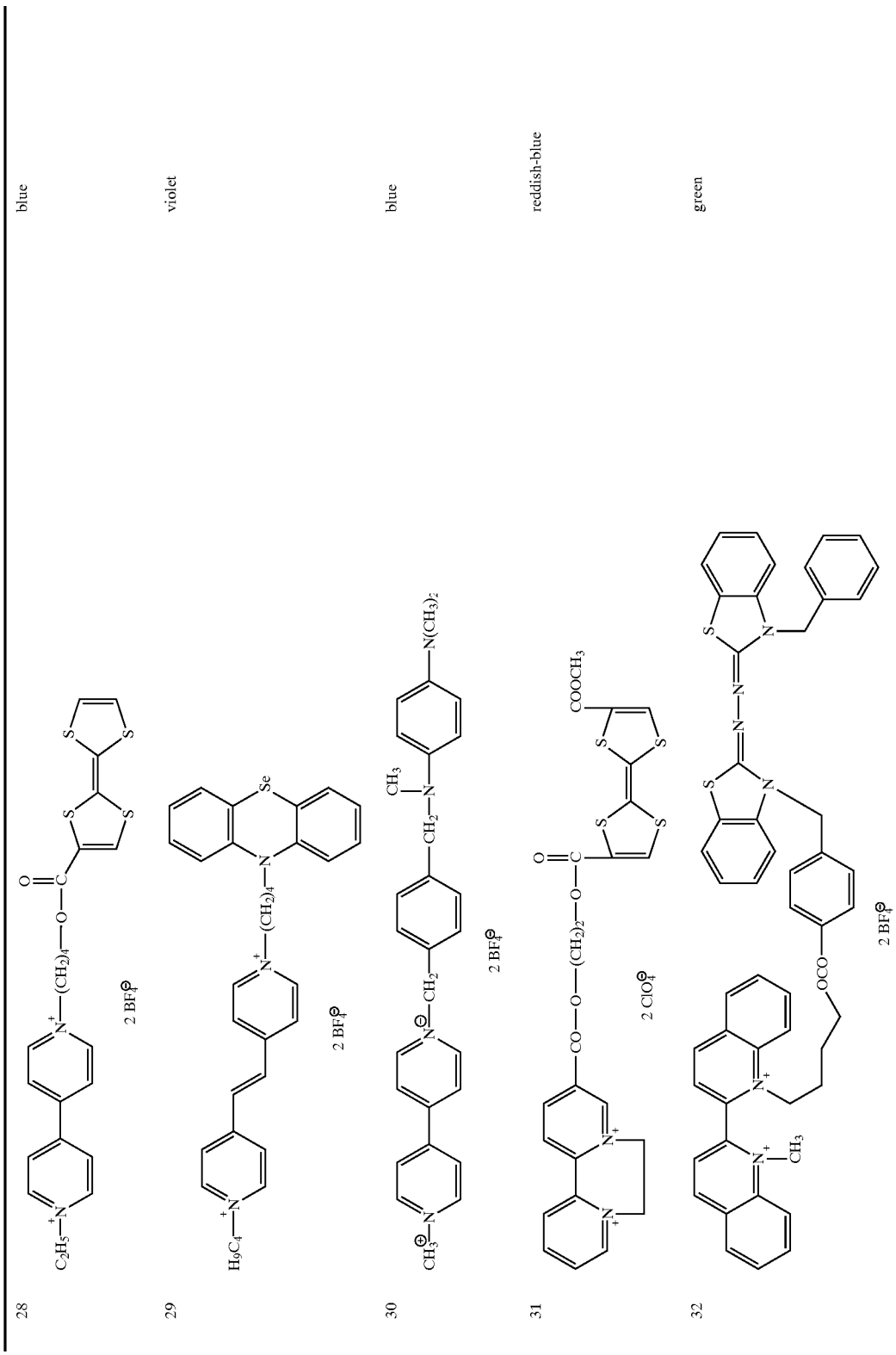

| | | |
|---|---|---|
| 33 | 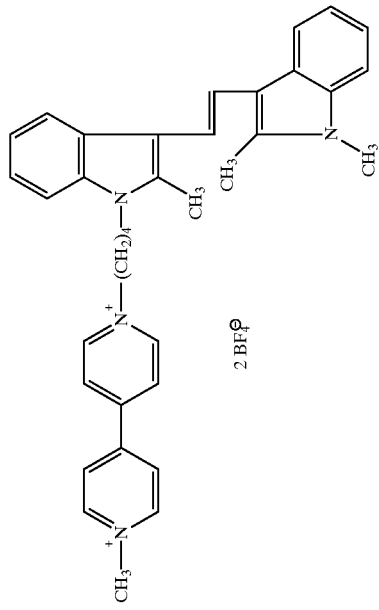 | violet |
| 34 | 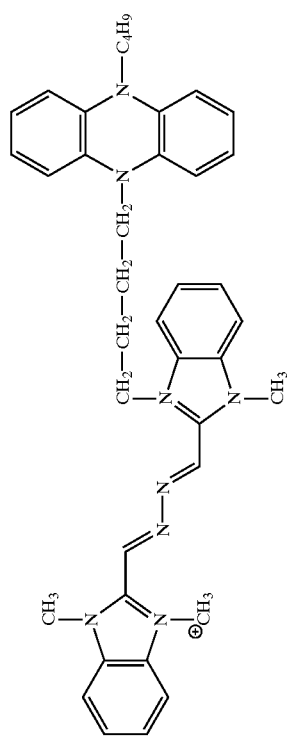 | green |
| 35 | 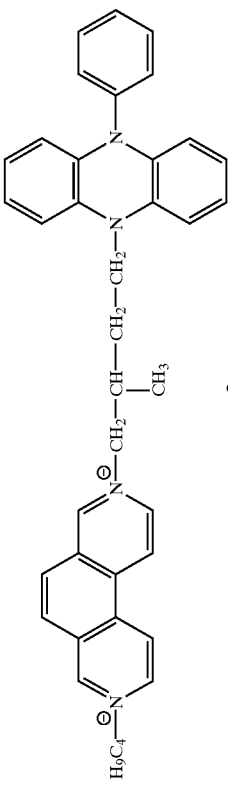 | green |

| | | |
|---|---|---|
| 36 | 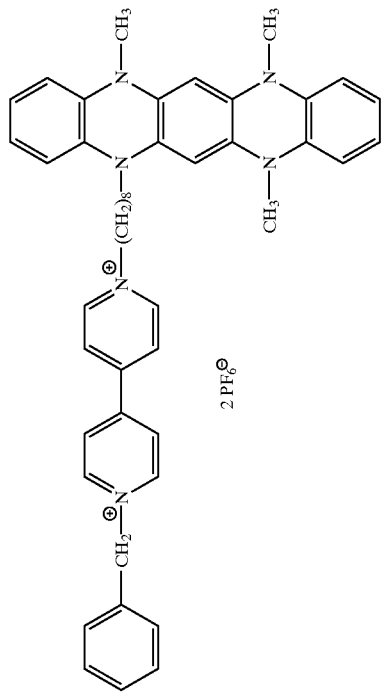 blue 2 PF$_6^\ominus$ | |
| 37 | 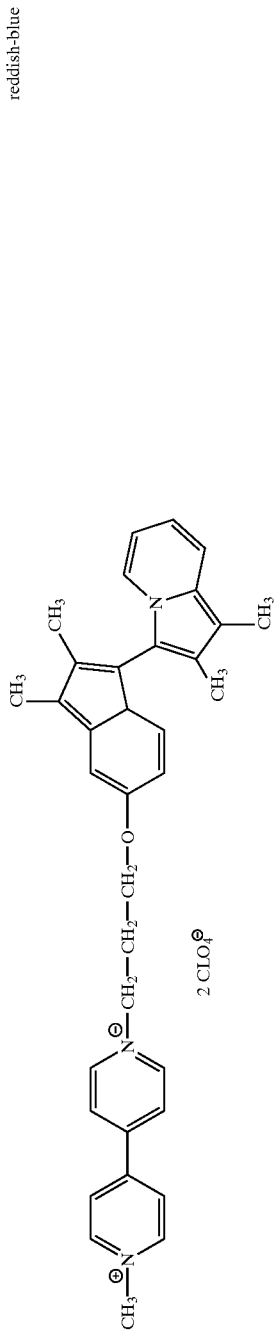 reddish-blue 2 ClO$_4^\ominus$ | |
| 38 | 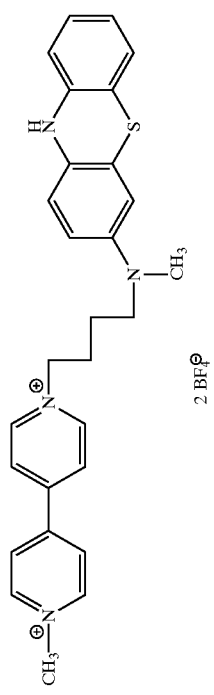 violet 2 BF$_4^\ominus$ | |

| | | |
|---|---|---|
| 39 | 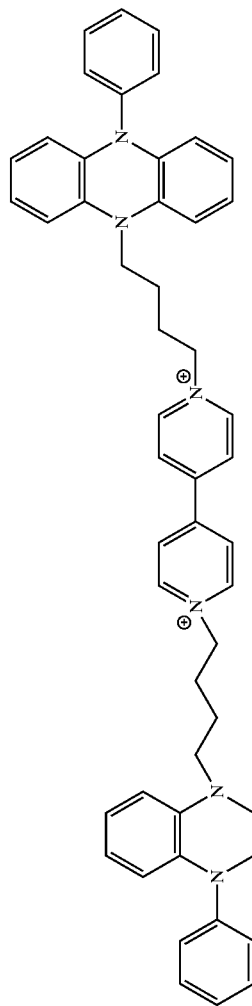 greenish blue | |
| 40 | 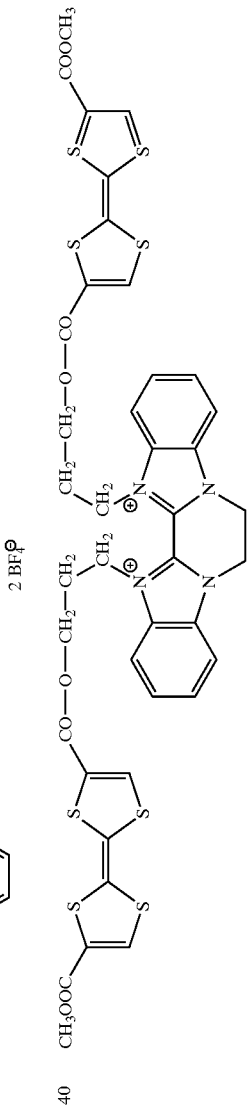 blue | |
| 41 | 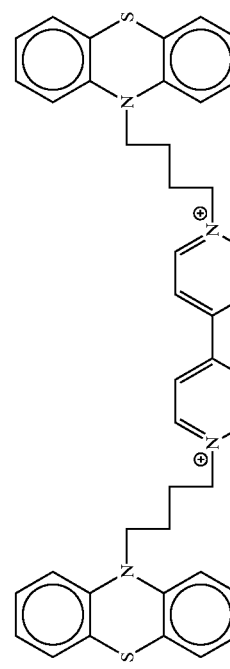 blue-violet | |

-continued
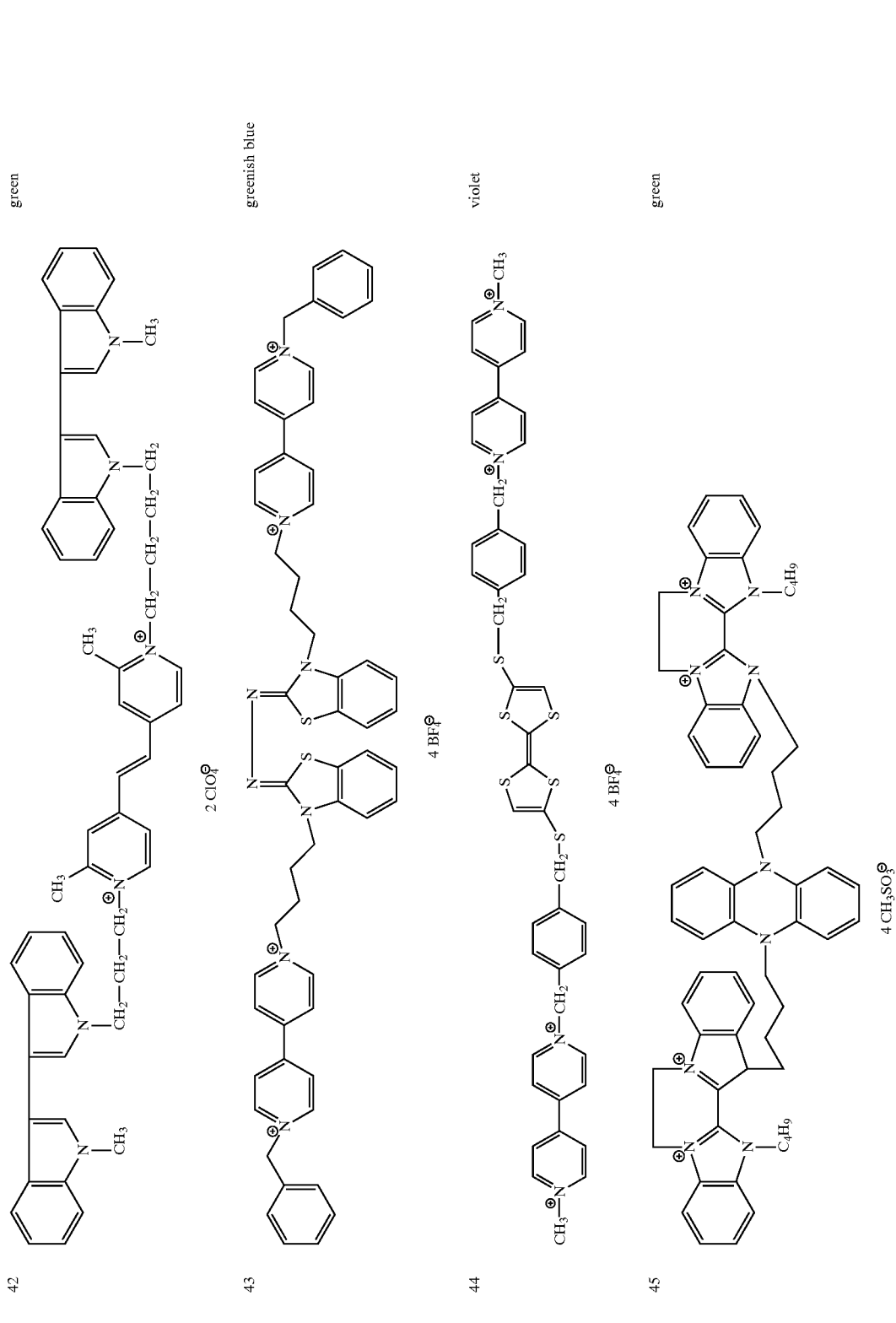

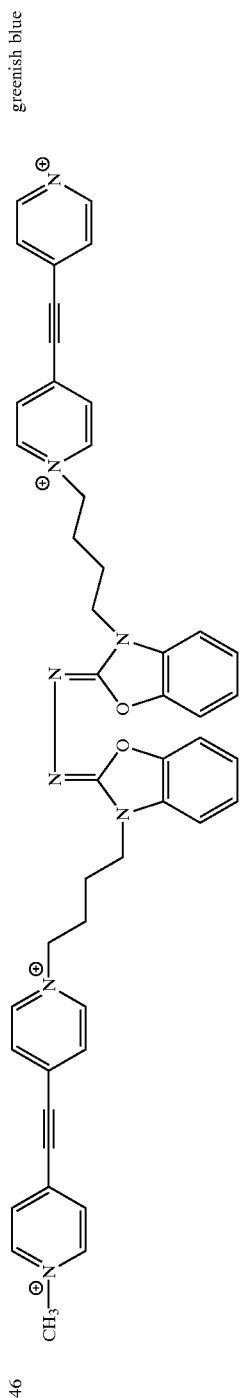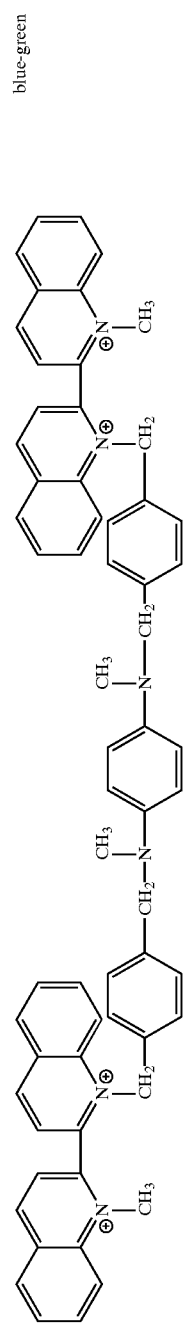
| Example | UV absorber |
|---|---|
| 22 | formula (CIIIa) |
| 23 | formula (CIV) |
| 24 | 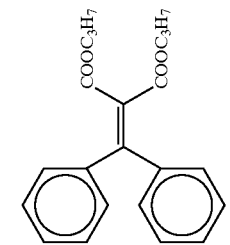 |
| 25 | formula (CIV) + (CV) |
| 26 | 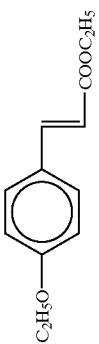 |
| 27 | formula (CV) |
| 28 | formula (CIII) + (CIV) + (CV) |

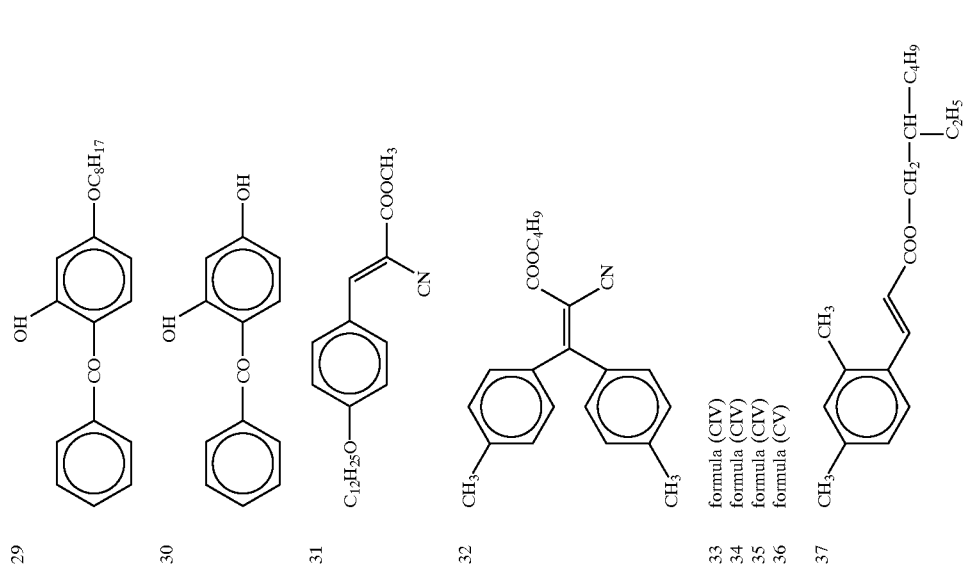

| | |
|---|---|
| 38 | (structure: 2-hydroxy-4-methoxyphenyl 4-methoxyphenyl ketone) |
| 39<br>40 | formula (CIV)<br>formula (CIV) |
| 41 | (structure: 2-hydroxy-4-propoxyphenyl phenyl ketone) |
| 42<br>43 | formula (CIII) + (CV)<br>formula (CIII) + (CV) |
| 44 | (structure: 2-hydroxy-4-methoxyphenyl 4-ethylphenyl ketone) |
| 45<br>46<br>47 | formula (CIV)<br>formula (CIV)<br>formula (CIV) |

What is claimed is:

1. A method for providing variable transmission in an electrochromic device comprising introducing into an electrochromic device a UV-protected electrochromic solution comprising
   (a) an electrochromic redox component comprising a weakly colored or colorless combination of at least one oxidizable substance $RED_1$ that releases electrons at an anode and in so doing undergoes transition into a substance $OX_1$ and at least one reducible substance $OX_2$ that accepts electrons at a cathode and in so doing undergoes transition into a substance $RED_2$, wherein at least one of $OX_1$ or $RED_2$ is accompanied by an increase in the absorbance in the visible region of the spectrum and thereby becomes colored and the combination is restored to the weakly colored or colorless form after charge equalization,
   with the proviso that at least one of the substances $RED_1$ is linked covalently to at least one of the substances $OX_2$ by a bridge; and
   (b) at least one UV absorber selected from the group consisting of unsubstituted and substituted cinnamic esters and unsubstituted and substituted 2-hydroxybenzophenones.

2. An electrochromic device containing a variable transmission medium comprising a UV-protected electrochromic solution comprising
   (a) an electrochromic redox component comprising a weakly colored or colorless combination of at least one oxidizable substance $RED_1$ that releases electrons at an anode and in so doing undergoes transition into a substance OX, and at least one reducible substance $OX_2$ that accepts electrons at a cathode and in so doing undergoes transition into a substance $RED_2$, wherein at least one of $OX_1$ or $RED_2$ is accompanied by an increase in the absorbance in the visible region of the spectrum and thereby becomes colored and the combination is restored to the weakly colored or colorless form after charge equalization,
   with the proviso that at least one of the substances $RED_1$ is linked covalently to at least one of the substances $OX_2$ by a bridge; and
   (b) at least one UV absorber selected from the group consisting of unsubstituted and substituted cinnamic esters and unsubstituted and substituted 2-hydroxybenzophenones.

3. An electrochromic device according to claim 2 configured as a cell, a window pane, a mirror, a sunroof, or a display device having electrically separate segments with individual electrical contacts.

4. An electrochromic device according to claim 2 consisting of two facing transparent glass or plastic plates in which the facing sides carry an electroconductive coating and between which is contained a UV-protected electrochromic solution comprising
   (a) an electrochromic redox component comprising a weakly colored or colorless combination of at least one oxidizable substance $RED_1$ that releases electrons at an anode and in so doing undergoes transition into a substance $OX_1$ and at least one reducible substance $OX_2$ that accepts electrons at a cathode and in so doing undergoes transition into a substance $RED_2$, wherein at least one of $OX_1$ or $RED_2$ is accompanied by an increase in the absorbance in the visible region of the spectrum and thereby becomes colored and the combination is restored to the weakly colored or colorless form after charge equalization,
   with the proviso that at least one of the substances $RED_1$ is linked covalently to at least one of the substances $OX_2$ by a bridge; and
   (b) at least one UV absorber selected from the group consisting of unsubstituted and substituted cinnamic esters and unsubstituted and substituted 2-hydroxybenzophenOnes.

5. An electrochrOmiC device according to claim 4 wherein one of the plates is mirrored.

6. An electrochromiC device according to claim 4 if that is subdivided into electrically separate segments, each of which contains the electrochromic solution.

* * * * *